(12) United States Patent
Carlier et al.

(10) Patent No.: US 6,472,408 B1
(45) Date of Patent: Oct. 29, 2002

(54) DIMERIC COMPOUNDS

(75) Inventors: Paul R. Carlier, Blacksburg, VA (US); Yifan Han, Kowloon (HK); Yuan-Ping Pang, Rochester, MN (US); Da-Ming Du, Beijing (CN)

(73) Assignee: The Hong Kong University of Science and Technology, Kowloon (HK)

( * ) Notice: Subject to any disclaimer, the term of this patent is extended or adjusted under 35 U.S.C. 154(b) by 0 days.

(21) Appl. No.: 09/784,034

(22) Filed: Feb. 16, 2001

(30) Foreign Application Priority Data

Feb. 16, 2000 (GB) ................................ 0003632

(51) Int. Cl.7 ..................... A61K 31/47; C07D 215/16; C07D 215/20
(52) U.S. Cl. ................. 514/312; 514/311; 514/314; 546/153; 546/157
(58) Field of Search ................ 546/153, 157; 514/311, 312, 314

(56) References Cited

PUBLICATIONS

CA 119:151639, abstract of Dorigo, J Med Chem, 1993, 36(17), pp 2475–2484.*
CA 127:229211, abstract of Mosti, Farmaco, 1997, 52(2), pp331–337.*
CA 68:78101, abstract of Pettit, J Org Chem 1968, 33(3), 1089–1092.*
CA 78:119099, abstract of Martin, J Med Chem, 1973, 16(2), pp 147–150.*
CA 117:171205, abstract of U.S. patent #5, 110, 815, 1992.*
CA 86:43586, abstract of Klar, Arch Pharm (Weinheim, Ger.), 1976, 309(7), 550–557.*
CA 120:134889, abstract of He, Chin Chem Lett, 1993, 4(7), 597–600.*
CA 122:265738, abstract of He, Zhongguo Yaowu Huaxue Zazhi, 1994, 4(4), 257–263.*
CA 123:285727, abstract of Fink, J Med Chem, 1995, 38(18), 3645–3651.*
CA 131:322816, abstract of Carlier, Bioorg Med Chem Lett, 1999, 9(16), 2335–2338.*
CA 133:135458, abstract of Carlier, Angew Chem, Int Ed, 2000, 39(10), 1775–1777.*

* cited by examiner

*Primary Examiner*—D. Margaret Seaman
(74) *Attorney, Agent, or Firm*—Burns, Doane, Swecker & Mathis, L.L.P.

(57) ABSTRACT

The invention relates to dimeric compounds comprising two 5-amino-5,6,7,8-tetrahydroquinoline fragments joined together by a divalent linking group, processes for their preparation, intermediates for their preparation, pharmaceutical compositions containing such dimeric compounds and the use of such compounds as cholinesterase inhibitors and in the treatment of neurodegenerative diseases, such as Alzheimer's Disease and myasthenia gravis.

56 Claims, No Drawings

DIMERIC COMPOUNDS

This application claims priority under 35 U.S.C. §§ 119 and/or 365 to 0003632.7 filed in Britain on Feb. 16, 2000; the entire content of which is hereby incorporated by reference.

BACKGROUND OF THE INVENTION

1. Field of the Invention

This invention relates to dimeric compounds comprising two 5-amino-5,6,7,8-tetrahydroquinoline fragments joined together by a divalent linking group, processes for their preparation, intermediates for their preparation, pharmaceutical compositions containing such dimeric compounds and the use of such compounds as cholinesterase inhibitors and in the treatment of neurodegenerative diseases, such as Alzheimer's Disease and myasthenia gravis.

2. Description of Related Art

Huperzine A is a selective and potent reversible acetylcholinesterase (AChE) inhibitor isolated from the club moss *Huperzia serrata* which shows considerable promise for the palliative treatment of Alzheimer's Disease.

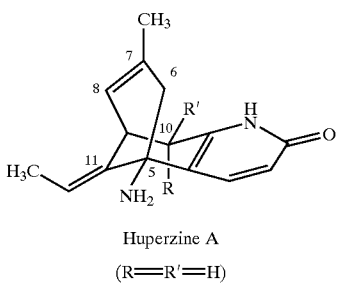

Huperzine A
(R═R'═H)

(A)

Total syntheses of the racemate and asymmetric syntheses of huperzine A have been reported (see for instance, Xia, Y.; Kozikowski, A. P; *J. Am. Chem. Soc.* 1989, 111, 4116–4117; Qian, L.; Ji, R.; *Tetrahedron Lett.* 1989, 30, 2089–2090; Yamada, F.; Kozikowski, A. P.; Reddy, E. R.; Pang, Y-P.; Miller, J. H.; McKinney, M.; *J. Am. Chem. Soc.* 1991, 113, 4695–4696; Kaneko, S.; Yoshino, T.; Katoh, T.; Terashima, S.; *Tetrahedron* 1998, 54, 5471–5484; and He, X.-C.; Wang, B.; Bai, D.; *Tetrahedron Lett.* 1998, 39, 411–414. However, these-syntheses require a minimum of 12 steps.

Enormous effort has also been directed towards the development of more easily synthesised analogues which might prove to. be. more potent than huperzine A. More than 100 such analogues have been disclosed in the scientific and patent literature. For instance, U.S. Pat. No. 5,929,084 discloses huperzine A derivatives in which the hydrogen atom at the 1-position in huperzine A is optionally replaced by a $C_{1-5}$ alkyl, pyridoyl or $C_{1-5}$ alkoxy-substituted benzoyl group and the amino group at the 5-position in huperzine A is replaced by a group —N(R")YR where Y is a carbonyl group, R" is a hydrogen atom or a $C_{1-5}$ alkyl group, or R" and Y together form a group ═CH, and R is a $C_{1-5}$ alkyl or an optionally substituted phenyl, benzyl, naphthyl or pyridyl group. U.S. Pat. No. 5,547,960 discloses huperzine A derivatives which are mono- or disubstituted at the 10-position. Substitution at other positions of the huperzine A molecule is also contemplated in U.S. Pat. No. 5,547,960 but no examples of any such compounds are provided. However, to date, the only huperzine A analogues which have shown superior potency relative to the natural product feature the judicious addition of one or two methyl groups at the 10-position. In this respect, the compounds of formula A above in which R is methyl and R' is hydrogen and both R and R' are methyl are 8- and 1.4-fold more potent than huperzine A respectively. However, the syntheses of these compounds are longer than that of the natural product.

Removal of the three carbon bridge (C-6 to C-8) from huperzine A has also been explored (see, for instance Kozikowski, A. P.; Miller, C. P.; Yamada, F.; Pang, Y-P.; Miller, J. H.; McKinney, M.; Ball, R. G.; *J. Med. Chem.* 1991, 34, 3399–3402; Bai. D.; *Pure & Appl. Chem.* 1993, 65, 1103–1112; and Fink. D. M.; Bores, G. M.; Effland, R. C.; Huger, F. P.; Kurys, B. E.; Rush, D. K.; Selk, D. E.; *J. Med. Chem.* 1995, 38, 3645–3651). However, in general, these derivatives are very weak AChE inhibitors ($IC_{50}$ generally >100,000 nM). Similarly, U.S. Pat. No. 5,110,815 discloses certain 5-amino-5,6,7,8-tetrahydroquinolines which are said to inhibit AChE and relieve memory dysfunction. However, the compounds disclosed are very weak AChE inhibitors ($IC_{50}$ values in the range of 3.1 to 9.6 μM).

Another AChE inhibitor which has been approved for use in the US for the palliative treatment of Alzheimer's Disease is 9-amino-1,2,3,4-tetrahydroacridine, also known as THA or tacrine. However, tacrine is a weaker AChE inhibitor than huperzine A and the use of tacrine is currently limited by its peripheral toxicity.

Various compounds have been synthesised which contain tacrine moieties in the search for further efficacious AChE inhibitors. For instance, U.S. Pat. No. 5,783,584 discloses certain alkylene-linked bis-tacrine compounds which are much more potent and much more selective for AChE inhibition than monomeric tacrine. However, despite the increased anti-AChE potency of these bis-tacrine compounds, the very presence of two tacrine moieties in such molecules is likely to cause some significant residual toxicity.

U.S. Pat. No. 5,886,007 discloses tacrine derivatives in which the amino group at the 9-position is substituted by an aralkyl group. These compounds also inhibit AChE but are generally less active than monomeric tacrine and 100- to 15000-fold less active than the compounds of U.S. Pat. No. 5,783,584.

Similarly, Carlier, P. R.; Du, D-M.; Han,Y.;Lin, J.; Pang, Y-P.; *Bioorg. Med. Chem. Lett.* 1999, 9, 2335–2338, discloses tacrine derivatives in which the amino group at the 9-position is attached to a 5-amino-5,6,7,8-tetrahydro-2 (1H)-quinolone moiety by an alkylene chain. However, whilst these compounds are stronger inhibitors of AChE than monomeric tacrine, they are not as potent as the compounds of U.S. Pat. No. 5,783,584. Moreover, like the compounds of U.S. Pat. No. 5,886,007, these compounds still contain one tacrine moiety and are therefore likely to exhibit toxicity problems.

DETAILED DESCRIPTION OF THE INVENTION

It has now been surprisingly discovered that dimeric compounds containing two 5-amino-5,6,7,8-tetrahydroquinoline or similar moieties joined together by a divalent linking group exhibit high potency as cholinesterase, especially AChE, inhibitors despite the fact that the activity of the constituent 5-amino-5,6,7,8-tetrahydroquinoline or similar monomers is extremely low. Indeed, the optimum dimers are twice as potent as huperzine A. Moreover, such dimeric compounds do not contain any toxic tacrine moieties and can be synthesised in just nine steps from commercially available starting materials.

According to the present invention there is therefore provided a dimeric compound comprising two fragments, which may be the same or different, joined together by a divalent linking group, each fragment having a nucleus of the general formula

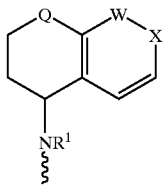

(I)

which may be substituted or unsubstituted, in which Q represents the number of carbon atoms necessary to form a 5,6 or 7-membered ring;

$R^1$ represents a hydrogen atom or an optionally substituted alkyl group;

—W—X— represents a group

—N($R^2$)—C(O)— or N=C(O$R^3$)—, where $R^2$ represents a hydrogen atom or an optionally substituted alkyl, alkenyl, alkynyl or aralkyl group, and $R^3$ represents a hydrogen atom or an optionally substituted alkyl or aralkyl group; or a salt thereof.

Suitable salts include acid addition salts and these may be formed by reaction of a suitable compound of formula I with a suitable acid, such as an o organic acid or a mineral acid, which is pharmaceutically acceptable. Pharmaceutically acceptable acid addition salts formed by reaction with a mineral acid are particularly preferred, especially salts formed by reaction with hydrochloric or hydrobromic acid. However, pharmaceutically acceptable acid addition salts formed by reaction with an organic acid are also preferred. Suitable organic acids include monobasic carboxylic acids, such as ethanoic and propanoic acid, dibasic carboxylic acids, such as maleic, tartaric, fumaric and oxalic acids, and tribasic carboxylic acids, such as carboxysuccinic and citric acid. Salts formed by reaction with tartaric, fumaric or oxalic acid are also preferred.

Any alkyl, alkenyl or alkynyl group, unless otherwise specified, may be linear or branched and may contain up to 12, preferably up to 6, and especially up to 4 carbon atoms. Preferred alkyl groups are methyl, ethyl, propyl and butyl. When an alkyl moiety forms part of another group, for example the alkyl moiety of an aralkyl group, it is preferred that it contains up to 6, especially up to 4, carbon atoms. Preferred alkyl moieties in this respect are methyl and ethyl.

An aryl group may be any aromatic monocylic or polycyclic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups, especially a phenyl. or naphthyl, and particularly a phenyl, group. When an aryl moiety forms part of another. group, for example the aryl moiety of an aralkyl group, it is preferred that it is a phenyl, naphthyl, anthryl, phenanthryl or pyryl, especially a phenyl or naphthyl, and particularly a phenyl, moiety.

An aralkyl group may be any alkyl group substituted by an aryl group. A preferred aralkyl group contains from 7 to 16, especially 7 to 11, carbon atoms, a particularly preferred aralkyl group being a benzyl group.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, haloalkyl, cycloalkyloxy, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido and heterocyclic groups. When any of the foregoing substituents represents or contains an alkyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms.

In a particularly preferred group of compounds Q represents one carbon atom which may be substituted or unsubstituted. Thus, the nucleus of general formula I is a 5-amino-5,6,7,8-tetrahydroquinoline moiety. Preferably, Q represents one carbon atom in both fragments of the dimeric compound. However, it is also envisaged that Q may represent a different number of carbon atoms in each fragment.

It is preferred that $R^1$ represents a hydrogen atom or a $C_{1-4}$ alkyl group, preferably unsubstituted. More preferably, $R^1$ represents a hydrogen atom.

In one preferred group of compounds —W—X— represents a group —N($^2$)—C(O)—. Preferably, $R^2$ represents a hydrogen atom or $C_{1-6}$ alkyl, $C_{2-6}$ alkenyl, $C_{2-6}$ alkynyl or $C_{7-6}$ aralkyl, preferably $C_{7-11}$ aralkyl, group More preferably, $R^2$ represents a hydrogen atom or a $C_{1-4}$ alkyl, especially methyl, group.

In another preferred group of compounds —W—X— represents a group —N=C(O$R^3$)—. Preferably, $R^3$ represents a hydrogen atom or a $C_{1-6}$ alkyl or $C_{7-6}$ aralkyl group. More preferably, $R^3$ represents a $C_{1-4}$ alkyl, especially methyl, or a $C_{7-11}$ aralkyl, especially benzyl group.

The saturated ring of the nucleus of general formula I may be unsubstituted. Alternatively, the saturated ring of the nucleus of general formula I may be substituted at one or more of the available carbon atoms by one or more substituents of formula $R^4$. Thus, the nucleus of general formula I may be further defined by the general formula

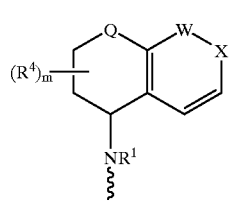

(IA)

in which Q, $R^1$ and —W—X— are as previously defined, m is 0 or an integer from 1 to (2p–5) where p is the number of carbon atoms in the saturated ring of the nucleus, and each substituent $R^4$ independently represents an optionally substituted alkyl or aralkyl group. Thus, when the saturated ring contains five carbon atoms (Q represents a single bond), m is 0 or an integer from 1 to 5; when Q represents one carbon atom, m is 0 or an integer from 1 to 7; and when Q represents two carbon atoms, m is 0 or an integer from 1 to 9. More preferably, m is 0 or an integer from 1 to 3. When the saturated ring of the nucleus of general formula I is substituted, it is preferred that two substituents $R^4$ are located at the 7-position of the nucleus and/or that one substituent $R^4$ is located at the 5-position of the nucleus. Preferably, each substituent $R^4$ independently represents a $C_{1-4}$ alkyl, especially a methyl, group.

It is preferred that the two fragments having a nucleus of the general formula I are the same as one another, that is, the dimeric compounds of the invention are homodimers. However, it is also envisaged that the two fragments having a nucleus of general formula I may be different from one another, that is, the dimeric compounds of the invention are heterodimers. In the case of heterodimers, the two fragments may differ only in optional substituents on the saturated ring of the nucleus or they may differ in fundamental size, structure and substituents as defined in relation to formula I.

The divalent linking group may be any group which is capable of linking the 5-amino groups of the two fragments having a nucleus of the general formula I. However, it is preferred that the divalent linking group is an optionally substituted alkylene chain which is optionally interrupted by one or more heteroatoms, such as oxygen, sulphur and nitrogen atoms, or optionally substituted aryl groups. Preferably, the optionally substituted alkylene chain is optionally interrupted by one or more moieties selected from —O—, —S—, —NR—, —CO— and optionally substituted aryl, especially $C_{6-14}$ aryl, groups, where R represents a hydrogen atom or an optionally substituted alkyl, preferably $C_{1-4}$ alkyl and especially methyl, group. More preferably, R represents a hydrogen atom.

It is particularly preferred that the optionally substituted alkylene chain is optionally interrupted by one or more moieties selected from —O—, —NH—, —C(O)—, phenyl and naphthyl groups. It is also preferred that the optionally substituted alkyl chain has a chain length of 2 to 16, preferably 4 to 14, and especially 6 to 12, atoms.

Preferably, the divalent linking group is an alkylene chain, a rigidified hydrocarbon linker, a polyethylene glycol linker, an oxalic diamide linker or a urea linker. A rigidified hydrocarbon linker is a hydrocarbon chain which is rigidified by the inclusion of an aryl moiety in the chain. A polyethylene glycol linker is a linker including one or more —O—CH$_2$—CH$_2$— units. An oxalic diamide linker is a linker including one or more —NH—C(O)—C(O)—NH— units. A urea linker includes one or more —NH—C(O)—NH— units. In the case of oxalic diamide and urea linkers, a —NH—C(O)—C(O)—NH— or —NH—C(O)—NH— unit must be separated from the 5-amino group of the fragments having a nucleus of the general formula I by at least two methylene groups. Also, if more than one —NH—C(O)—C(O)—NH— or —NH—C(O)—NH— unit is present in the divalent linking group, the units must be separated from one another by at least two methylene groups.

Especially preferred divalent linking groups include optionally substituted alkylene groups of formula —(CH$_2$)$_n$— where n is an integer from 2 to 16, preferably 4 to 14 and especially 6 to 12; rigidified hydrocarbon linkers of formula —(CH$_2$)$_q$—Ar—(CH$_2$)$_r$— where q and r are each independently 0 or an integer from 1 to 5, preferably 1 to 4 and especially 1 or 2, and Ar represents an optionally substituted $C_{6-14}$ aryl, preferably $C_{6-10}$ aryl and especially phenyl or naphthyl, group; and of formula —(CH$_2$)$_s$—Ar$^1$—B—Ar$^2$—(CH$_2$)$_t$— where s and t are each independently 0 or an integer from 1 to 3, especially 1 or 2, Ar$^1$ and Ar$^2$ each independently represent an optionally substituted $C_{6-14}$ aryl, preferably $C_{6-10}$ aryl and especially phenyl or naphthyl, group and B represents a group —(CH$_2$)$_u$— where u is 0,1,2 or 3, especially 0 or 2, —CH=CH— or —C≡C—; polyethylene glycol linkers of formula —CH$_2$CH$_2$—(OCH$_2$CH$_2$)$_v$— where v is an integer from 1 to 4, especially 2 or 3; oxalic diamide linkers of formula —(CH$_2$)$_w$—NH—C(O)—C(O)—NH—(CH$_2$)$_x$— where w and x independently represent an integer from 2 to 6, preferably 2 to 5 and especially 3 to 5; and urea linkers of formula —(CH$_2$)$_y$—[NH—C(O)—NH—(CH$_2$)$_z$]$_a$— where y and z independently represent an integer from 2 to 6, especially 3 to 5, and a represents an integer from 1 to 3.

Specific preferred linkers include the following:

rigidified hydrocarbon linkers

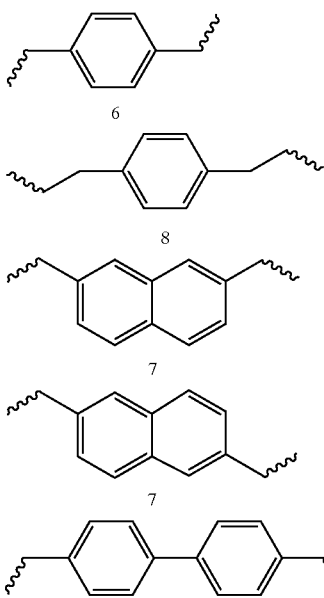

6

8

7

7

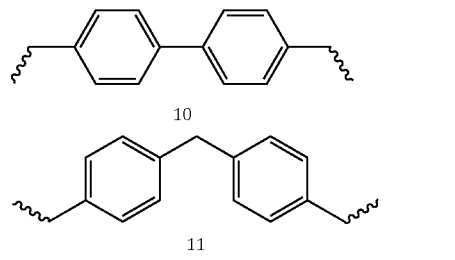

10

11

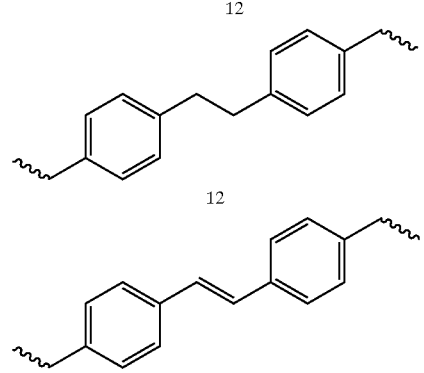

12

12

12

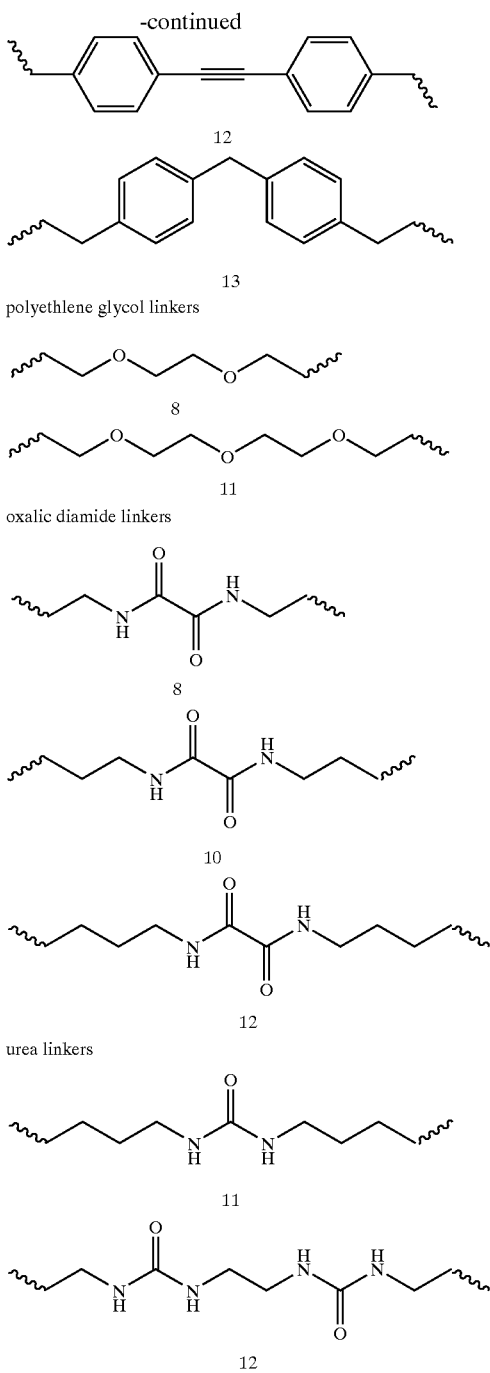

polyethlene glycol linkers oxalic diamide linkers urea linkers

The numbers given above indicate the effective chain length of the divalent linking group.

Although the divalent linking groups shown above have been shown as containing one or more methylene groups —CH$_2$—, each of these methylene groups may be optionally substituted by any of the optional substituents listed above, preferably C$_{1-4}$ alkyl, and especially methyl, groups. However, it is preferred that these divalent linking groups are unsubstituted.

Preferably, the divalent linking group is an unsubstituted alkylene chain of formula —(CH$_2$)$_n$— in which n is an integer from 2 to 16, preferably 4 to 14, and especially 6 to 12, carbon atoms. It is particularly preferred that n is an integer from 9 to 12.

In a particularly preferred sub-group of the dimeric compounds of the invention, both fragments are the same, Q represents an unsubstituted carbon atom, R$^1$ represents a hydrogen atom, —W—X— represents a group —N(R$^2$)—C(O)— where R$^2$ represents a hydrogen atom or a methyl group, the saturated ring of the nucleus of formula I is unsubstituted or substituted at the 7-position by two methyl groups and/or at the 5-position by one methyl group, and the divalent linking group is an unsubstituted alkylene chain of formula —(CH$_2$)$_n$— where n is an integer from 4 to 14.

N,N'-Di-5'-(5',6',7',8'-tetrahydroquinolin-2-onyl)-1,12-diaminododecane, N,N'-di-5'-(5',6',7',8'-tetrahydroquinolin-2-onyl)-1,13-diaminotridecane and salts thereof are especially preferred.

In another particularly preferred sub-group of the dimeric compounds of the invention, both fragments are the same, Q represents an unsubstituted carbon atom, R$^1$ represents a hydrogen atom, —W—X— represents a group —N=C(OR$^3$)— where R$^3$ represents a methyl or benzyl group, the saturated ring of the nucleus of formula I is unsubstituted or substituted at the 5-position by one methyl group, and the divalent linking group is an unsubstituted alkylene chain of formula —(CH$_2$)$_n$— where n is an integer from 4 to 14, preferably 10 or 12.

N,N'-Di-5'-(5',6',7',8'-tetrahydro-2'-methoxyquinolinyl)-1,10-diaminodecane, N,N'-di-5'-(5',6',7',8'-tetrahydro-2'-methoxyquinolinyl)-1,12-diaminododecane and salts thereof are especially preferred.

It should also be appreciated that the fragments having a nucleus of general formula I contain chiral centres and the dimeric compounds of the invention are therefore capable of existing as different optical isomers. Moreover, if these fragments or the divalent linking group contain an alkenyl group, the dimeric compounds are also capable of existing as different geometric isomers. The present invention thus includes both the individual isomers and mixtures of such isomers. Enantiomers of the dimeric compounds of the invention are particularly preferred, especially the (S,S)- and (R,R)-enantiomers. However, (R,S)-stereoisomers may be present in a mixture with the racemic mixture of (S,S)- and (R,R)-enantiomers and are also included within the present invention.

The present invention also provides a process for the preparation of a dimeric compound according to the invention as defined above which comprises. reacting two compounds, which may be the same or different, having a nucleus of the general formula

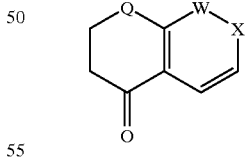

(II)

which may be substituted or unsubstituted, in which Q and —W—X— are as defined above, or a salt thereof, with a compound of the general formula

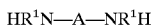  (III)

in which each R$^1$ is independently as defined above and A represents a divalent linking group as defined above and, either reducing the bis-imine compound so formed to produce a dimeric compound as defined above which is unsubstituted at the 5-position, or reacting the bis-imine compound so formed with a suitable organometallic reagent to produce a dimeric compound as defined above which is substituted at the 5-position; and, if desired, when —W—X— represents a group —N═C(OR³)— and R³ represents an optionally substituted arylmethyl group in at least one of the compounds having a nucleus of general formula II, subjecting the dimeric compound so formed to hydrogenolysis to produce a dimeric compound in which both moieties —W—X— represent a group —N(R²)—C(O)—.

The reaction of the two compounds having a nucleus of formula II with the compound of formula III may be conveniently carried out in the presence of a suitable solvent. Suitable solvents include aromatic solvents, such as benzene or toluene. Preferably, the reaction is carried out at the reflux temperature of the solvent, preferably in the presence of a catalyst, such as ethanoic acid, to form the bis-imine compound in situ.

Reduction of the bis-imine compound to produce a dimeric compound which is unsubstituted at the 5-position is carried out by reaction with a suitable reducing agent. Suitable reducing agents include sodium borohydride in methanol.

Alternatively, suitable organometallic reagents for reacting with the bis-imine compound to form a dimeric compound which is substituted at the 5-position include organolithium reagents and Grignard reagents. This reaction may be carried out in the presence or absence of a suitable Lewis acid depending on the organometallic reagent selected. If required, suitable Lewis acids include boron trifluoride, aluminium chloride and titanium tetrachloride.

Hydrogenolysis of dimeric compounds which contain a group —N═C(OR³)—, where R³ represents an optionally substituted arylmethyl group in at least one of the compounds having a nucleus of formula II, to produce a dimeric compound in which both moieties —W—X— represent a group —N(R²)—C(O)— may be carried out using a suitable hydrogenating agent, such as hydrogen gas in the presence of palladium on carbon, in a suitable solvent, such as ethanol. Preferably, R³ represents a benzyl group.

Compounds having a nucleus of formula II in which —W—X— represents a group —N(R²)—C(O)— where R² is a hydrogen atom may be conveniently prepared by condensing a compound having a nucleus of the general formula

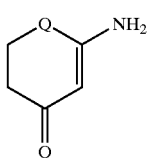

(VI)

in which Q is as defined above, with methyl propiolate according to the methods of Dubas-Sluyter, M. A. T.; Speckarnp, W. N.; Huisman H. O.; *Recueil*, 1972, 91,157–160 and Zacharias, G.; Wolfbeis, O. S.; Junek, H.; *Monatsch, Chem.*, 1974, 105, 1283–1291. The reaction is preferably carried out at a temperature in the range of 100 to 180, preferably 110 to 170° C.

Compounds having a nucleus of formula VI may be conveniently prepared by reacting a compound having a nucleus of the general formula

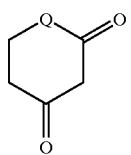

(VII)

in which Q is as defined above, with ammonia in a suitable solvent, such as benzene or toluene, suitably at reflux temperature.

Compounds having a nucleus of formula II in which —W—X— represents a group —N(R²)—C(O)— where R² is other than a hydrogen atom may be prepared by reacting a compound having a nucleus of formula II in which —W—X— represents a group —N(R²)—C(O)— where R² is a hydrogen atom with a compound of formula R²'Y where R²' is a suitable alkyl, alkenyl, alkynyl or aralkyl group and Y represents a suitable halogen atom in the presence of sodium methoxide and a suitable solvent, such as tetrahydrofuran, at reflux temperature.

Compounds having a nucleus of formula II in which —W—X— represents a group —N═C(OR³)— where R³ is as defined above may be prepared by reacting a compound having a nucleus of formula II in which —W—X— represents a group —N(R²)—C(O)—, where R² is a hydrogen atom, with a compound of formula R³Y where R³ is as defined above and Y is a suitable halogen atom. The reaction is conveniently carried out in the presence of silver carbonate in a suitable solvent, such as trichloromethane or toluene. Preferably, the reaction is carried out at room temperature, that is 15 to 35° C., preferably 20 to 30° C.

Compounds of formulae III and VII are known compounds or can be prepared by methods analogous to known processes.

In another aspect, the present invention provides a process for the preparation of a dimeric compound according to the invention as defined above which comprises reacting two compounds, which may be the same or different, having a nucleus of the general formula

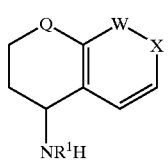

(IV)

which may be substituted or unsubstituted, in which Q, R¹ and —W—X— are as defined above, or a salt thereof, with a compound of the general formula

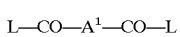

L—CO—A¹—CO—L (V)

in which each L independently represents a hydrogen atom or a leaving group Y of which the conjugate acid HY has a pKa value which is less than or equal to 10 and —CO—A¹—CO— represents a group which forms a divalent linking group as defined above in the resultant dimeric compound; if desired, reducing the dimeric compound so formed to produce a further dimeric compound as defined above;

and, if desired, when —W—X— represents a group —N═C(OR³)— and R³ represents an optionally substituted arylmethyl group in at least one of the compounds having a nucleus of general formula IV, subjecting the dimeric compound so formed to hydrogenolysis to. produce a dimeric compound in which both moieties —W—X— represent a group —N(R²)—C(O)—. This process is particularly suitable for preparing dimeric compounds which are substituted at the 5-position by substituent R⁴.

The reaction of the two compounds having a nucleus of formula IV with the compound of formula V may be conveniently carried out in the presence of a suitable solvent. Suitable solvents include aromatic solvents, such as benzene. Preferably, the reaction is carried out in the presence of a catalyst, such as ethanoic acid, preferably at the reflux temperature of the reaction mixture.

When L is a hydrogen atom, a bis-imine is formed in situ which can be reduced to produce a dimeric compound according to the invention using a suitable reducing agent, such as sodium borohydride in methanol, as described above. However, when L is other than a hydrogen atom, for instance a chlorine atom, no reduction is required.

Hydrogenolysis of dimeric compounds which contain a group —N=C(OR³)—, where R³ represents an optionally substituted arylmethyl group in at least one of the compounds having a nucleus of formula IV to produce a dimeric compound in which both moieties —W—X— represent a group —N(R²)—C(O)— may be carried out as described above.

Compounds having a nucleus of formula IV which bear a substituent at the 5-position in which —W—X— represents a group —N=C(OR³)—, where R³ represents an optionally substituted arylmethyl group, may be conveniently prepared by reacting a compound having a nucleus of formula II in which —W—X— represents a group —N=(OR³)—, where R³ represents an optionally substituted arylmethyl group, with a suitable Grignard reagent in a suitable solvent, such as tetrahydrofuran, at a suitable temperature, such as room temperature, that is, 15 to 35° C., preferably 20 to 30° C. The resultant tertiary alcohol compound may then be reacted with O-arylmethylhydroxylamine in a suitable solvent, such as toluene, in the presence of trifluoroethanoic acid at a suitable temperature, such as room temperature. The desired compound may then be obtained by treating the resultant compound with borane-tetrahydrofuran at a temperature in the range from 0° C. to the reflux temperature of the reaction mixture.

Compounds having a nucleus of formula IV which bear no substituent at the 5-position and in which —W—X— represents a group —N=C(OR³), where R³ represents an optionally substituted arylmethyl group, may be conveniently prepared by reacting a compound having a nucleus of formula II in which —W—X— represents a group —N=C(OR³)—, where R³ represents an optionally substituted arylmethyl group, with hydroxylamine or O-benzylhydroxylamine in pyridine, and subsequent reduction with active metal reducing agents (such as Raney Nickel and hydrogen gas) or borane respectively.

Compounds of formulae V are known compounds or can be prepared by methods analogous to known processes.

U.S. Pat. No. 5,110,815 discloses some compounds having a nucleus of the general formula II, namely, 5,6,7,8-tetrahydro-5-oxo-2-(phenylmethoxy)quinoline; 5,6,7,8-tetrahydro-5-oxo-2(1H)-quinolinone; 5,6,7,8-tetrahydro-1-methyl-5-oxo-2(1H)-quinolinone; 5,6,7,8-tetrahydro-5-oxo-1-(2-propenyl)-2(1H)-quinolinone; 5,6,7,8-tetrahydro-5-oxo-1-phenylmethyl-2(1H)-quinolinone; 5,6,7,8-tetrahydro-7,7-dimethyl-5-oxo-2(1H)-quinolinone; 1,7,7-trimethyl-5-oxo-2(1H)-quinolinone; 5,6,7,8-tetrahydro-1-propyl-5-oxo-2(1H)-quinolinone; 1-hexyl-5,6,7,8-tetrahydro-5-oxo-2(1H)-quinolinone; 5,6,7,8-tetrahydro-1-(3-methyl-2-butenyl)-5-oxo-2(1H)-quinolinone and 5,6,7,8-tetrahydro-5-oxo-1-(2-phenylethyl)-2(1H)-quinolinone. However, certain compounds having a nucleus of general formula II are novel. The present invention therefore also provides a compound having a nucleus of the general formula

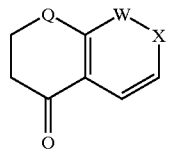

(II)

which may be substituted or unsubstituted, or a salt thereof, in which Q and —W—X— are as defined above; with the provisos that (i) when Q represents one carbon atom, —W—X— represents a group —N=C(OR³)— and the nucleus of formula II is unsubstituted, then R³ does not represent a benzyl group;

(ii) when Q represents one carbon atom, —W—X— represents a group —N(R²)—C(O)— and the nucleus of formula II is unsubstituted, then R² does not represent a hydrogen atom or a methyl, propyl, hexyl, 2-propenyl, 3-methyl-2-butenyl, benzyl or 2-phenylethyl group; and (iii) when Q represents one carbon atom, —W—X— represents a group —N(R²)—C(O)— and the nucleus of formula II is substituted at the 7-position by two methyl groups, then R² is not a hydrogen atom or a methyl group.

Compounds in which Q represents one carbon atom and —W—X— represents a group —N=C(OR³)— where R³ represents a methyl group are particularly preferred. Of these, 5,6,7,8-tetrahydro-2-methoxy-5-oxo-quinoline and salts thereof are especially preferred.

U.S. Pat. No. 5,110,815 also discloses some compounds having a nucleus of the general formula IV, namely 5,6,7,8-tetrahydro-5-methyl-2-(phenylmethoxy)-5-quinolinamine hemifumarate; 5,6,7,8-tetrahydro-5-amino-5-methyl-2(1H)-quinolinone hydrochloride; 5,6,7,8-tetrahydro-5-amino-1,5-dimethyl-2(1H)-quinolinone; 5,6,7,8-tetrahydro-N,5-dimethyl-2-(phenylmethoxy)-5-quinolinamine; 5,6,7,8-tetrahydro-5-methyl-5-(methylamino)-2(1H)-quinolinone hydrochloride; 5,6,7,8-tetrahydro-2-(phenylmethoxy)-5-(phenylmethyl)-5-quinolinamine; 5-amino-5,6,7,8-tetrahydro-5-(phenylmethyl)-2(1H)-quinolinone hydrochloride; 5,6,7,8-tetrahydro-5-[-(2-phenyethyl)amino]-2(1H)-quinolinone hydrochloride; 5,6,7,8-tetrahydro-1-methyl-5-[(2-phenylethyl)amino]-2(1H)-quinolinone dihydrochloride monohydrate; 5,6,7,8-tetrahydro-5-oxo-2-(phenylmethoxy)quinoline oxime benzyl ether; 5,6,7,8-tetrahydro-5-[(2-phenylethyl)amino]-1-(2-propenyl)-2(1H)-quinolinone; 5-[[2-(3,4-dichlorophenyl)ethyl]amino]-5,6,7,8-tetrahydro-1-(2-propenyl)-2(1H)-quinolinone fumarate; 5,6,7,8-tetrahydro-5-[(2-phenylethyl)-amino]-1-propyl-2(1H)-quinolinone fumarate; 5-[[2-(3,4-dichlorophenyl)-ethyl]amino]-5,6,7,8-tetrahydro-1-(phenylmethyl)-2(1H)-quinolinone fumarate; 5,6,7,8-tetrahydro-1-methyl-5-[(phenylmethyl)amino]-2(1H)-quinolinone fumarate; 5-[[2-(4-trifluromethylphenyl)ethyl]amino]-5,6,7,8-tetrahydro-1-methyl-2(1H)-quinolinone; 5,6,7,8-tetrahydro-1-methyl-5-[[2-(4-nitrophenyl)ethyl]amino]-2(1H)-quinolinone; 5-[[2-(4-chlorophenyl)ethyl]amino]-5,6,7,8-tetrahydro-1-methyl-2(1H)-quinolinone; 5,6,7,8-tetrahydro-5-[[2-(4-methoxyphenyl)ethyl]amino]-1-methyl-2(1H)-quinolinone;

5,6,7,8-tetrahydro-1-methyl-5-[[2-(4-methylphenyl)-ethyl] amino]-2(1H)-quinolinone fumarate; 5-[[2-(2,4-dichlorophenyl)ethyl]amino]-5,6,7,8-tetrahydro-1-methyl-2 (1H)-quinolinone; 5-[[2-(3,4-dichlorophenyl)ethyl]-amino]-5,6,7,8-tetrahydro-1-methyl-2(1H)-quinolinone; 5,6,7,8-tetrahydro-1-methyl-5-[[2-(2,2-diphenyl)ethyl]amino]-2 (1H)-quinolinone; 5,6,7,8-tetrahydro-1-methyl-5-[(3-phenylpropyl)amino]-2(1H)-quinolinone flumarate; 5-[[2-(4-chlorophenyl)-ethyl]amino]-5,6,7,8-tetrahydro-1,7,7-trimethyl-2(1H)quinolinone fumarate; 5-[[2-(3,4-dichlorophenyl)ethyl]amino]-5,6,7,8-tetrahydro-1-propyl-2 (1H)-quinolinone; 5,6,7,8-tetrahydro-1-methyl-5-[[2-(1-naphthyl)ethyl]amino]-2(1H)-quinolinone fumarate; 5-[[2-(4-chlorophenyl)ethyl]amino]-5,6,7,8-tetrahydro-1-(2-propenyl)-2(1H)-quinolinone hydrochloride; 5-[[2-(4-chlorophenyl)ethyl]amino]-5,6,7,8-tetrahydro-1-propyl-2 (1H)-quinolinone fumarate; 5-[[2-(3,4-dichlorophenyl) ethyl]amino]-1-hexyl-5,6,7,8-tetrahydro-2(1H)-quinolinone fumarate; 5-[[2-(3,4-dichlorophenyl)ethyl]amino]-5,6,7,8-tetrahydro-1-(3-methyl-2-butenyl)-2(1H)-quinolinone maleate; 5,6,7,8-tetrahydro-1-methyl-5-[[2-(2-napthyl) ethyl]amino]-2(1H)-quinolinone and 5-[[2-(3,4-dichlorophenyl)ethyl]amino]-5,6,7,8-tetrahydro-1-(2-[phenylethyl)-2(1H)-quinolinone. In addition, *Bioorg. Med. Chem. Lett.* 1999, 9, 2335–2338 (ibid) discloses 5-amino-, 5-n-butylamino- and 5-2-(phenyl)ethyl-5,6,7,8-tetrahydro-2 (1H)-quinolinones which also fall within formula IV. However, certain compounds having a nucleus of general formula IV are novel. In another aspect, the present invention therefore provides a compound having a nucleus of the general formula

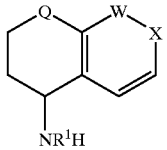

(IV)

which may be substituted or unsubstituted, or a salt thereof, in which Q, $R^1$ and —W—X— are as defined above; with the provisos that (i) when Q represents one carbon atom, —W—X— represents a group —N($R^2$)—C(O)— where $R^2$ represents a hydrogen atom or a group —N=C($OR^3$)— where $R^3$ represents a benzyl group and the nucleus of formula IV is substituted at the 5-position by a methyl or benzyl group, then $R^1$ is not a hydrogen atom;

(ii) when Q represents one carbon atom, —W—X— represents a group —N($R^2$)—C(O)— where $R^2$ represents a hydrogen atom or a group —N=C($OR^3$)— where $R^3$ represents a benzyl group and the nucleus of formula IV is substituted at the 5-position by a methyl group, then $R^1$ is not a methyl group;

(iii) when Q represents one carbon atom, —W—X— represents a group —N($R^2$)—C(O)— where $R^2$ represents a methyl group and the nucleus of formula IV is substituted at the 5-position by a methyl group, then $R^1$ is not a hydrogen atom;

(iv) when Q represents one carbon atom, —W—X— represents a group —N($R^2$)—C(O)— where $R^2$ represents a methyl group and the nucleus of formula IV is unsubstituted, then $R^1$ is not a benzyl, 2-phenylethyl, 2-(4-trifluoromethylphenyl)-ethyl, 2-(4-nitrophenyl) ethyl, 2-(4-chlorophenyl)ethyl, 2-(4-methoxyphenyl) ethyl, 2-(4-methylphenyl)ethyl, 2-(2,4-dichlorophenyl) ethyl, 2-(3,4-dichlorophenyl)ethyl, 2-(2,2-diphenyl) ethyl, 2-(1-naphthyl)ethyl or 3-phenylpropyl group;

(v) when Q represents one carbon atom, —W—X— represents a group —N($R^2$)—C(O)— where $R^2$ represents a propyl or 2-propenyl group and the nucleus of formula IV is unsubstituted, then $R^1$ is not a 2-phenylethyl, 2-(4-chlorophenyl)ethyl or 2-(3,4-dichlorophenyl)ethyl group;

(vi) when Q represents one carbon atom, —W—X— represents a group —N($R^2$)—C(O)— where $R^2$ represents a hydrogen atom and the nucleus of formula IV is unsubstituted, then $R^1$ is not a hydrogen atom, n-butyl or 2-phenylethyl group;

(vii) when Q represents one carbon atom, —W—X— represents a group —N($R^2$)—C(O)— where $R^2$ represents a hexyl, 3-methyl-2-butenyl, benzyl or 2-phenylethyl group and the nucleus of formula IV is unsubstituted then $R^1$ is not a 2-(3,4-dichlorophenyl) ethyl group; and (viii) when Q represents one carbon atom, —W—X— represents a group —N($R^2$)—C(O)— where $R^2$ represents a methyl group and the nucleus of formula IV is substituted at the 7-position by two methyl groups, then $R^2$ is not a 2-(4-chlorophenyl)ethyl group.

Compounds in which $R^1$ is a hydrogen atom are preferred and compounds in which a compound as defined above in which Q represents one carbon atom, $R^1$ represents a hydrogen atom and —W—X— represents a group —N=C ($OR^3$)— where $R^3$ represents a benzyl group are particularly preferred. Of these, (±)-2-benzyloxy-5,6,7,8-tetrahydro-5-quinolinamine and salts thereof are especially preferred.

It should also be appreciated that compounds having a nucleus of general formula IV contain chiral centres and are therefore capable of existing as different optical isomers. The present invention thus also includes both the individual isomers and mixtures of such isomers. Moreover, U.S. Pat. No. 5,110,815 makes no mention of the possibility of such isomers and *Bioorg. Med. Chem. Lett.*, 1999, 9, 2335–2338 only discloses racemic mixtures of such compounds. Thus, the invention also provides an enantiomer of a compound having a nucleus of the general formula

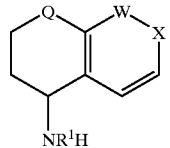

(IV)

which may be substituted or unsubstituted, or a salt thereof, in which Q, $R^1$ and —W—X— are as first defined above without provisos. The invention also provides the (S)- and (R) enantiomers of such compounds. Enantiomers in which $R^1$ is a hydrogen atom are preferred, particularly enantiomers in which Q represents one carbon atom, $R^1$ represents a hydrogen atom and —W—X— represents a group —N=C($OR^3$)—, where $R^3$ represents a benzyl group. Of these, (S)-2-benzyloxy-5,6,7,8-tetrahydro-5-methyl-5-quinolinamine; (R)-2-benzyloxy-5,6,7,8-tetrahydro-5-methyl-5-quinolin-amine; (S)-(+)-2-benzyloxy-5,6,7,8-tetrahydro-5-quinolinamine and (R)-(−)-benzyloxy-5,6,7,8-tetrahydro-5-quinolinamine and salts thereof are especially preferred.

The enantiomerically pure compounds having a nucleus of general formula IV can be prepared from the corresponding racemic mixtures using conventional resolution techniques. One such technique involves the reaction of the racemic mixture with a pure enantiomer of an optically active acid, such as mandelic acid, in a suitable solvent, for instance, an alcohol such as methanol or ethanol. The desired enantiomerically pure compound may then be recrystallised from the solution. Enantiomerically pure dimeric compounds of the invention may be prepared from the appropriate enantiomerically pure compounds having a nucleus of general formula IV by reaction with a suitable compound of formula V.

The invention also provides a pharmaceutical composition which comprises a carrier and, as active ingredient, a dimeric compound as defined above. A process for the preparation of a pharmaceutical composition is also provided which comprises bringing a dimeric compound as defined above into association with a carrier.

A pharmaceutically acceptable carrier may be any material with which the active ingredient is formulated to facilitate administration. A carrier may be a solid or a liquid, including a material which is normally gaseous but which has been compressed to form a liquid, and any of the carriers normally used in formulating pharmaceutical compositions may be used. Preferably, compositions according to the invention contain 0.5 to 95% by weight of active ingredient.

The dimeric compounds of the invention can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

The dimeric compounds and compositions of the invention are also useful as cholinesterase inhibitors and inhibit both acetylcholinesterase (AChE) and butyrylcholinesterase (BChE). However, they are more active against AChE than BChE. The invention therefore also provides a dimeric compound or a composition as defined above for use as a cholinesterase inhibitor or for use in the treatment of a condition which is ameliorated by cholinesterase inhibition. Such conditions include neurodegenerative diseases, especially Alzheimer's Disease and myasthenia gravis. Indeed, the dimeric compounds and compositions of the invention are particularly useful for relieving the memory dysfunction associated with Alzheimer's. Disease. A suitable dosage for the dimeric compounds and compositions of the invention in the treatment of, for example, Alzheimer's Disease is from 0.02 to 0.20 mg, preferably 0.05 to 0.15 mg, once or twice daily, assuming that the patient has an average body weight of 50 kg.

Use of a dimeric compound or a composition as defined above for the manufacture of a medicament for use as a cholinesterase inhibitor or in the treatment of a condition which is ameliorated by cholinesterase inhibition is also provided. Similarly, a method for inhibiting cholinesterase activity in a mammal afflicted with a condition which is ameliorated by cholinesterase inhibition which comprises administering to the mammal in need thereof an amount of a compound as defined above or a composition as defined above effective to inhibit said activity is also provided.

The invention is further illustrated by the following examples. In these examples, $^1$H and $^{13}$C-NMR spectra were recorded on a BRUKER ARX-300 spectrometer ($^1$H at 300.13 MHz, $^{13}$C at 75.48 MHz). All chemical shifts are expressed in ppm and the coupling constants in Hz. Melting points were determined with Electrothermal 9100 melting point apparatus and are uncorrected. Chemical ionization (CI) mass spectra were acquired using either ammonia or methane as the reagent gas. Elemental analyses were performed by Shanghai Institute of Organic Chemistry, Chinese Academy of Sciences (Shanghai, P. R. C.). Optical rotation was measured with Perkin Elmer 241 Polarimeter. Analytical thin-layer chromatography (TLC) was performed with aluminum sheets coated with RDH silica gel 60 F254. Flash column chromatography was performed using Merck silica gel 60 (230–400 mesh). High-performance liquid chromatography (HPLC) was performed on Lichrosorb® RP Select B column (0.4×25 cm, 5 $\mu$m), detection at 303 or 337 nm, gradient elution using solvent mixtures of A=$H_2O$+0.1% $CF_3COOH$, B=20% A+80% $CH_3CN$ operated at the program of A: B=100:0 at 0 minutes to 10:90 at 30 minutes, flow rate 1.0 m/min.

All moisture-sensitive reactions were conducted in oven dried (150° C.) glassware under an atmosphere of dry nitrogen. Gastight syringes were dried in vacuo at room temperature before use in these reactions. Tetrahydrofuran was distilled from sodium-benzophenone ketyl immediately prior to use. All chemicals were commercial products and were used as received.

EXAMPLE 1

Preparation of rac-/meso-N',N'-Di-5'-(5',6',7',8'-Tetrahydroquinolin-2-onyl)-1,7-diaminoheptane, bis-Hydrochloride Salt (rac-/meso-13d.2HCl) (Formula IA: Q=—$CH_2$—; $R^1$=H; —W—X—=—N($R^2$)—C(O)—; $R^2$=H; m=0; Divalent Linking Group=—$(CH_2)_n$—; n=7)

5,6,7,8-Tetrahydro-5-oxo-2(1H)-quinolinone (5) (653 mg. 4.0 mmol) prepared according to the method of Dubas-Sluyter, M. A. T.; Speckamp, W. N.; Huisman, H. O. *Recueil* 1972, 91, 157–160, 1,7-diaminoheptane (260 mg, 2.0 mmol) and 5 drops of acetic acid in benzene (50 mL) were refluxed with azeotropic removal of water for 24 hrs. The resulting solution was cooled, the solvent was removed in vacuo, and the resulting schiff base was reduced without further purification by the following procedure. After being ground to a fine powder, the schiff base was suspended in methanol (50 mL). To this suspension was added dropwise a solution of sodium borohydride (289 mg, 7.6mmol). The mixture was stirred at room temperature for 12 hours. The fine precipitate formed was filtered, washed with methanol and water. The mother liquor was concentrated, purified by passing through a silica plug (elution with methanol-ammonium hydroxide 50:1), and the filtrate concentrated to afford another portion of precipitate. In total 425 mg of rac-/meso-13d (50% based on ketone) free amine was obtained. mp 218–219° C. $^1$H NMR (CD$_3$OD): δ 1.36 (s, 6H), 1.45–1.58 (m, 4H), 1.68–2.00 (m, 8H), 2.48–2.68 (m, 8H), 3.62 (t, J=4.8 Hz, 2H), 6.35 (d, J=9.3 Hz, 2H), 7.59 (d, J=9.3 Hz, 2H). $^3$C NMR (CD$_3$OD): δ 17.10, 26.32, 26.92, 29.02, 29.99, 46.20, 52.28, 115.37, 116.75, 142.66, 143.61, 162.37; CIMS (NH$_3$): m/e 425 (M+1), 295, 278, 165, 148.

200 mg free amine was dissolved in methanolic HCl solution (10 mL) and ethyl acetate was added to inititate precipitation. Following several days standing at room temperature, filtration afforded rac-/meso-13d.2HCl (177 mg, 67% based on free amine). mp 189–191° C. (Dec.) $^1$H NMR (CD$_3$OD): δ 1.45 (s, 6H), 1.75 (s, br, 4H), 1.90–2.09 (m, 6H), 2.16–2.28 (m, 2H), 2.62–2.80 (m, 4H), 2.96–3.18 (m, 4H), 4.32 (d, J=4.0 Hz, 2H), 6.43 (d, J=9.4 Hz, 2H), 7.66 (d, J=9.4 Hz, 2H); HPLC (area%): 17.6 min. 99.9%. Analysis: Calcd. for C$_{25}$H$_{36}$N$_4$O$_2$.2HCl.3.5H$_2$O: C, 53.57; H, 8.09; N, 9.99. Found: C, 53.81; H, 7.93; N, 9.86.

EXAMPLE 2

Preparation of rac-/meso-N,N'-Di-5'-(7',7'-Dimethyl-5',6',7',8'-tetrahydroquinolin-2-onyl)-1,7-diaminoheptane, bis-Fumaric Acid Salt (rac-/meso-14d.2.1 Fumaric Acid) (Formula IA; Q=—CH$_2$—; R$^1$=H; —W—X—=—N(R$^2$)—C(O)—; R$^2$=H; m=2: R$^4$=7,7-(CH$_3$)$_2$; Divalent Linking Group=—(CH$_2$)$_n$—; n=7)

7,7-Dimethyl-5,6,7,8-tetrahydro-5-oxo-2(1H)-quinolinone (6) prepared according to Zacharias, G.; Wolfbeis, O. S.; Junek, H. Monatsh. Chem. 1974, 105, 1283–1291, 1,7-diaminoheptane (143 mg, 1.1 mmol) and 5 drops of acetic acid in benzene (30 mL) were refluxed with azeotropic removal of water for 48 hours. The resulting solution was cooled, the solvent was removed in vacuo, and the schiff base was reduced as follows. After being ground to a fine powder and suspended in methanol (30 mL), a solution of sodium borohydride (166 mg, 4.4 mmol) in methanol (5 mL) was added dropwise. The mixture was stirred at room temperature for 12 hours. The fine precipitate formed was filtered, washed with methanol and water. The mother solution was concentrated and water (20 mL) was added to the residue to get another portion of precipitate, which was washed with 50% methanol in Water (10 mL) and dried. Crystallization from dichloromethane-ethyl acetate gave rac-/meso-14d (185 mg, 35% based on ketone), mp 207–208° C. $^1$H NMR (CDCl$_3$): δ 0.94 (s, 6H), 1.10 (s, 6H), 1.26–1.42 (m, 8H), 1.42–1.55 (m, 4H), 1.90 (dd, J=4.9, 12.4 Hz, 2H), 2.40 (d, J=17.3 Hz, 2H), 2.50–2.71 (m, 6H), 3.61 (dd, J=5.9, 8.9 Hz, 2H), 6.44 (d, J=9.3 Hz, 2H), 7.73 (d, J=9.3 Hz, 2H); $^{13}$C NMR (CDCl$_3$): δ 25.37, 27.38, 29.48, 30.71, 30.77, 31.28, 40.32, 43.10, 45.98, 51.83, 116.43, 117.01, 142.01, 143.22, 165.26; CIMS (CH$_4$): m/e 481 (M+1,5), 351 (45), 306 (50), 193 (90), 176 (100), 131 (35).

The bis-fumaric acid salt was prepared by dissolving rac-/meso-14d (100 mg, 0.21 mmol) in minimum amount of methanol, and adding fumaric acid (49 mg, 0.42 mmol) in a minimum amount of methanol. After several days standing at room temperature gave rac-/meso-14d.2.1 fumaric acid (130 mg, 80% based on free amine) was collected by filtration, mp 161.5–163° C. $^1$H NMR (D$_2$O): δ 0.92 (s, 6H), 1.16 (s, 6H), 1.36 (s, 6H), 1.60–1.80 (m, 6H), 2.09–2.18 (m, 2H), 2.42 (d, J=17.6 Hz, 2H), 2.68 (d, J=17.6 Hz, 2H), 2.98–3.12 (m, 4H), 4.55 (dd, J=7.2, 9.7 Hz, 2H), 6.56 (d, J=9.4 Hz, 2H), 6.65 (s, 4H), 7.79 (d, J=9.4 Hz, 2H). $^{13}$C NMR (CD$_3$OD): δ 24.93, 27.87, 27.95, 30.17, 31.65, 32.22, 39.18, 41.44, 45.54, 54.81, 110.19, 119.50, 136.86, 142.49, 148.31, 165.83, 172.10. HPLC (area%): 16.5 min. 97.7%. Analysis: Calcd. for C$_{29}$H$_{44}$N$_4$O$_2$.2.1C$_4$H$_4$O$_4$.3H$_2$O: C, 57.70; H, 7.56; N, 7.20. Found: C, 57.75; H, 7.16; N, 7.35. The $^1$H NMR integration also matched the proposed stoichiometry.

EXAMPLE 3

Preparation of rac/meso-N,N'-di-5'-(5',6',7',8'-Tetrahydro-1'-methyl-quinolinolyl)-1,10-diaminodecane, bis-Fumaric Acid (rac-/meso-15 g.2 Fumaric Acid) (Formula IA: Q=—CH$_2$—; R$^1$=H; —W—X—=—N(R$^2$)—C(O)—; R$^2$=—CH$_3$; mn=0; Divalent Linking Group=—(CH$_2$)$_n$—; n=10)

(a) Preparation of 5,6,7,8-Tetrahydro-1-methyl-5-oxo-2-quinolinone (7)

A mixture of compounds (0.65 g, 4 mmol), methyl iodide (2.8 g, 20 mmol) and sodium methoxide (0.22 g, 4 mmol) in 50 mL of dry tetrahydrofuran was refluxed for 4 hours. The reaction mixture was diluted with water (30 mL), the layers were separated, and the aqueous phase was extracted with dichloromethane (3×30 mL). The combined organic phase was washed once with brine (20 mL), dried with anhydrous magnesium sulfate and concentrated to give the crude product. Crystallization from ethyl acetate afforded compound 7 (0.5 g, 71%) as pale crystals, mp 174–175.5° C. $^1$H NMR (CD$_3$OD): δ 2.16 (quin, J=6.2 Hz, 2H), 2.51 (t, J=6.2 Hz, 2H), 3.05 (t, J=6.2 Hz, 2H), 3.58 (s, 3H), 6.44 (d, J=9.5 Hz, 1H), 7.97 (d, J=9.5 Hz, 1H); $^{13}$C NMR (CD$_3$OD): δ 22.68, 28.95, 32.10, 37.48, 116.84, 118.09, 138.21, 160.76, 165.90, 197.23. IR (KBr): v 1670, 1542, 1422, 1300, 1080, 844, 762 cm$^{-1}$. EIMS: m/e: 177 (M$^+$, 100), 148 (60), 121 (50), 93 (38); Analysis: Calcd. for C$_{10}$H$_{11}$NO$_2$.0.2H$_2$O: C, 66.43; H, 6.36; N, 7.75. Found: C, 66.19; H, 6.22; N, 7.60.

(b) Preparation of rac-/meso-N,N'-di-5'-(5',6',7',8'-Tetrahydro-1'-methyl-quinolinolyl)-1,10-diaminodecane, bis-Fumaric Acid (rac-/meso-15 g.2 Fumaric Acid)

5,6,7,8-Tetrahydro-1-methyl-5-oxo-2-quinolinone (7) (496 mg, 2.8 mmol) prepared as described in (a) above, 1,10-diaminodecane (240 mg, 1.4 mmol) and 5 drops of acetic acid in benzene (50 mL) were reacted and reduced as described in Examples 1 and 2 above to afford rac-/meso-15 g (339 mg, 49%), mp 106.5–108° C. $^1$H NMR (CDCl$_3$): δ 1.29 (s, br, 12H), 1.40–1.55 (m, 4H), 1.58–1.72 (m, 2H), 1.73–1.90 (m, 4H), 1.90–2.05 (m, 2H), 2.45–2.73 (m, 8H), 3.48 (s, 6H), 3.54 (t, J=4.2 Hz, 2H), 6.47 (d, J=9.3 Hz, 2H), 7.34 (d, J=9.3 Hz, 2H); $^{13}$C NMR (CDCl$_3$): δ 17.58, 26.38, 27.35, 27.47, 29.51, 30.20, 30.50, 47.34, 53.87, 117.27, 117.48, 140.69, 144.65, 163.23; CIMS (CH$_4$): m/e 495 (M+1, 20), 334 (35), 179 (95), 162 (100);

The fumaric acid salt was prepared as described in Example 2 above: free base (198 mg, 0.4 mmol) afforded rac-/meso-15 g.2 fumaric acid (242 mg, 77% based on free amine), mp 156–157° C. $^1$H NMR (CD$_3$OD): δ 1.32 (s, br, 12H), 1.63–1.78 (m, 4H), 1.90–2.08 (m, 6H), 2.18–2.28 (m, 2H), 2.72–3.13 (m, 8H), 3.54 (s, 6H), 4.32 (s, 2H), 6.48 (d, J=9.3 Hz, 2H), 6.56 (s, 4H), 7.59 (d, J=9.3 Hz, 2H); $^{13}$C NMR (CD$_3$OD): δ 18.00, 25.00, 27.81, 28.11, 28.33, 30.61, 30.70, 31.67, 47.26, 56.67, 112.05, 117.97, 136.75, 143.02, 151.15, 165.69, 171.79; HPLC (area %): 17.3 min. 99.0%. Analysis: Calcd. for C$_{30}$H$_{46}$N$_4$O$_2$.2C$_4$H$_4$O$_4$.3H$_2$O: C, 58.45; H, 7.74; N, 7.17. Found: C, 58.64; H, 7.72; N. 7.16. The $^1$H NMR integration also matched the proposed formulation.

EXAMPLE 4

Preparation of 5-n-Butylamino-5,6,7,8-tetrahydroquinolinone, bis-Hydrochloride [(±)-16.2HCl] (Formula IV: Q=—CH$_2$—; R$^1$=nC$_4$H$_9$: —W—X—=—N(R$^2$)—C(O)—; R$^2$=H; Unsubstituted Compound 5 (0.65 g, 4.0 mmol) and n-butylamine (0.73 g, 10 mmol) were reacted and reduced as described in Example 1 above for rac-/meso-13d to give (±)-16 (0.45 g, 51%), mp 159–161° C. $^1$H NMR (CD$_3$OD): δ 0.93 (t, J=7.2 Hz, 31H), 1.38 (sextet, J=7.4 Hz, 2H), 1.45–1.55 (m, 2H), 1.68–1.82 (m, 2H), 1.82–2.20 (m, 2H), 2.48–2.72 (m, 2H), 3.61 (t, J=4.7 Hz, 1H), 6.35 (d, J=9.3 Hz, 1H), 7.59 (d, J=9.3 Hz, 1H); $^{13}$C NMR (CD$_3$OD): δ 14.85, 18.85, 22.15, 28.06, 28.40, 33.50, 47.88, 54.42, 118.02, 119.13, 145.61, 146.47, 166.13; ESIMS: m/e 221 (M+1, 95), 180 (25), 148 (84).

The hydrochloride salt was prepared as above: 150 mg free base afforded (±)-16.2HCl (165 mg, 78%), mp 124–126° C. $^1$H NMR (D$_2$O): δ 0.94 (t, J=7.4 Hz, 3H), 1.41 (Sextet, J=7.4 Hz, 2H), 1.70 (quin, J=7.4 Hz, 2H), 1.82–2.10 (m, 3H), 2.18–2.27 (m, 1H), 2.69–2.88 (m, 2H), 3.03–3.20 (m, 2H), 4.41 (t, J=4.0 Hz, 1H), 6.56 (d, J=9.3 Hz, 1H), 7.73 (d, J=9.3 Hz, 1H); HPLC (area%): 16.1 min. 99.8%. Analysis: Calcd. for C$_{13}$H$_{20}$N$_2$O.2HCl.0.8H$_2$O: C, 50.75; H, 7.73; N, 9.11. Found: C, 50.60; H, 7.85; N, 8.98.

EXAMPLE 5

Preparation of rac-/meso-N,N'-di-5'-(5',6',7',8'-Tetrahydro-2'-methoxy-quinolinyl)-1,10-diaminodecane, bis-Fumaric Acid (rac-/meso-17 g.2 Fumaric Acid) (Formula IA; Q=—CH$_2$—; R$^1$=H, —W—X—=—N=C(OR$^3$)—; R$^3$=—CH$_3$; m=0: Divalent Linking Group=—(CH$_2$)$_n$—; n=10)

(a) Preparation of 5,6,7,8-Tetrahydro-2-methoxy-5-oxo-quinoline (8) (Formula II: Q=—CH$_2$—; —W—X—=—N=C(OR$^3$)—; R$^3$=—CH$_3$)

A mixture of compound 5 (8.2 g, 50 mmol) prepared as described in Example 1, methyl iodide (15.7 mL, 250 mmol), and silver carbonate (8.3 g, 30 mmol) in 150 mL of chloroform was stirred in a flask at room temperature for 48 hours. The reaction mixture was filtered through celite, and the filtrate was concentrated in vacuo, and purified by column chromatography (elution with hexanes-ethyl acetate 3:1) to give compound 8 (7.2 g, 81%) as a light yellow solid, mp 101–102° C. $^1$H NMR (CDCl$_3$): δ 2.15 (quin, J=6.4 Hz, 2H), 2.62 (t, J=6.6 Hz, 2H), 3.01 (t, J=6.2 Hz, 2H), 3.99 (s, 3H), 6.65 (d, J=8.7 Hz, 1H), 8.15 (d, J=8.7 Hz, 1H); $^{13}$C NMR (CDCl$_3$): δ 22.01, 32.49, 38.20, 53.89, 109.83, 122.73, 137.62, 163.89, 166.11, 197.08. FABMS: m/e 178 (M+1, 100), 154 (16), 137 (26). Analysis: Calcd. for C$_{10}$H$_{11}$NO$_2$: C, 67.78; H, 6.26; N, 7.90. Found: C, 67.94; H, 6.36; N, 7.91.

(b) Preparation of rac-/meso-N,N'-di-5'-(5',6',7',8'-Tetrahydro-2'-methoxy-quinolinyl)-1,10-diaminodecane, bis-Fumaric Acid (rac-/meso-17 g.2 Fumaric Acid)

5,6,7,8-Tetrahydro-2-methoxy-5-oxo-quinoline (8) (496 mg, 2.8 mmol) prepared as described in (a) above, 1,10-diaminodecane (241 mg, 1.4 mmol) and 5 drops of acetic acid were reacted and reduced as described in Example 1 above to afford rac-/meso-17 g (375 mg, 54%), mp 59–60.5° C. $^1$H NMR (CDCl$_3$): δ 1.13 (s, br, 2H), 1.29 (s, br, 12H), 1.40–1.56 (m, 4H), 1.70–1.90 (m, 6H), 1.90–2.05 (m, 2H), 2.55–2.88 (m, 8H), 3.69 (t, J=4.7 Hz, 2H), 3.88 (s, 6H), 6.53 (d, J=8.4 Hz, 2H), 7.55 (d, J=8.4 Hz, 2H). $^{13}$C NMR (CDCl$_3$): δ 17.71, 27.32, 28.07, 29.46, 30.49, 32.26, 47.00, 53.12, 54.44, 107.73, 127.08, 139.51, 154.59, 162.17. CIMS (CH$_4$): m/e 495 (M+1), 334, 185, 162, 93.

The fumaric acid salt was prepared as described in Example 2 above: free base (150 mg, 0.3 mmol) afforded rac-/meso-17 g.2 fumaric acid (190 mg, 87% based on free amine), mp 178–179.5° C. $^1$H NMR (D$_2$O): δ 1.20–1.40 (m, 12H), 1.66 (quin, J=7.3 Hz, 4H), 1.86–2.13 (m, 6H), 2.15–2.25 (m, 2H), 2.73–2.95 (m, 4H), 3.00–3.15 (m, 4H), 3.91 (s, 6H), 4.48 (t, J=4.1 Hz, 2H), 6.58 (s, 4H), 6.82 (m, J=8.7 Hz, 2H), 7.81 (d, J=8.7 Hz, 2H). $^{13}$C NMR (CD$_3$OD): δ 18.54, 25.91, 27.22, 27.57, 29.96, 30.18, 32.04, 46.68, 55.78, 56.45, 108.85, 120.49, 136.42, 143.14, 158.38, 165.75, 172.64. HPLC (area%): 20.2 min. 96.7%. Analysis: Calcd. for C$_{30}$H$_{46}$N$_4$O$_2$.2C$_4$H$_4$O$_4$: C, 62.79; H, 7.49; N, 7.71. C, 62.65; H, 7.51; N, 7.76. The $^1$H NMR integration also matched the proposed formulation.

EXAMPLE 6

Preparation of rac-/meso-N,N'-di-5'-(5',6',7',8'-Tetrahydro-2'-benzyloxy-5'-methoxyquinolinyl)-1,10-diaminodecane (rac-/meso-18 g) (Formula IA: Q=—CH$_2$—; R$^1$=H; —W—X—=—N=C(OR$^3$)—; R$^3$=Benzyl; m=1: R$^4$=5—CH$_3$; Divalent Linking Group=—(CH$_2$)$_n$—; n=10)

(a) Preparation of Sebacic Dialdehyde (Formula V: L=H: A$^1$=—(CH$_2$)$_n$—; n=8)

A solution of dichloromethane (25 mL) and oxalyl chloride (2.8 g, 22 mmol) in a 100-ml flask was cooled. with dry ice-acetone bath. The dimethyl sulfide (3.4 g, 44 mmol) dissolved in dichloromethane (5 mL) was added to the stirred oxalyl chloride solution at −50 to −60° C. The reaction mixture was stirred for 2 minutes, and the 1,10-decanediol (10 mmol in 10 ml of tetrahydrofuran, add a minimum amount of dimethyl sulfide to dissolve the alcohol) was added within 5 minutes. Stirring was continued for an additional 45 minutes, triethylamine (13.9 ml, 100 mmol) was added. The reaction mixture was stirred for 5 minutes and then allowed to warm to room temperature. After 1 hour, water (50 mL) was then added and the aqueous layer was reextracted with additional dichloromethane (50 mL). The organic layer was combined, washed with saturated sodium chloride solution (100 mL), and dried over anhydrous magnesium. The solvent was removed in vacuo to give the crude oily product. Purification by column chromatography on silica gel (elution with dichloromethane) to afford 1.5 g (88%) of a light yellow oil. $^1$H NMR (CDCl$_3$): δ 1.32 (s, 8H), 1.52–1.68 (m, 4H), 2.43 (dt, J=1.8, 7.3 Hz, 4H), 9.77 (t, J=1.8 Hz, 2H). $^{13}$C NMR (CDCl$_3$): δ 21.97, 29.01, 29.08, 43.82, 202.76. CIMS (C$_4$H$_{10}$) m/e: 171 (M+1).

(b) Preparation of 2-Benzyloxy-5,6,7,8-tetrahydro-5-oxo-quinoline (9) (Formula II; Q=—CH$_2$—; —W—X—=—N=C(OR$^3$): R$^3$=benzyl)

This was prepared according to the method of Fink, D. M.; Bores, G. M.; Effland, R. C.; Huger, F. P.; Kurys, B. E.; Rush, D. K.; Selk, D. E. *J. Med. Chem.* 1995, 38, 3645–3651.

(c) Preparation of 2-Benzyloxy-5,6,7,8-tetrahydro-5-hydroxy-5-methyl-quinoline (10)

Methylmagnesium iodide (10 mL, 30 mmol, 3.0 M solution in diethyl ether) was added dropwise to a solution of compound 9 (7.6 g, 30 mmol) prepared as described in (b) above in 300 mL of toluene at room temperature. The exothermic reaction:was controlled with an ice. water bath. The resulting solution was stirred at room temperature for 0.5 hours, and then it was quenched by the addition of saturated ammonium chloride solution. The layers were separated, and the aqueous phase was extracted with ethyl acetate (3×100 mL). The combined organic layers were washed with brine (50 mL), dried over anhydrous magnesium sulfate, filtered, and concentrated to give crude product. Purification by column chromatography on silica gel (elution with ethyl acetate-hexanes 1:3) provided 6.5 g (80%) of desired alcohol as light yellow oil. $^1$H NMR (CDCl$_3$): δ 1.52 (s, 3H), 1.71 (s, 1H), 1.82–2.00 (m, 4H), 2.72–2.90 (m, 2H), 5.34 (s, 2H), 6.65 (d, J=8.7 Hz, 1H), 7.26–7.39 (m, 3H), 7.46 (d, J=7.3 Hz, 2H), 7.77 (d, J=8.7 Hz, 1H). $^{13}$C NMR (CDCl$_3$): δ 19.88, 30.25, 32.64, 39.47, 67.46, 70.32, 109.14, 127.72, 128.10, 128.37, 130.71, 137.44, 137.53, 153.59, 161.95. CIMS (NH$_3$): m/e: 270 (M+1), 252.

(d) Preparation of 2-Benzyloxy-5-benzyloxyamino-5,6,7,8-tetrahdro-5-methyl-quinoline (11)

Trifluoroacetic acid (0.9 g, 7.9 mmol)) was added to a solution of compound 10 (2.1 g, 7.8 mmol) prepared as described in (c) above and O-benzylhydroxylamine (2.5 g, 20.3 mmol) in 40 mL of toluene at room temperature. The resulting mixture was stirred at room temperature for 24 hours, and then it was poured over ice and basified with concentrated ammonium hydroxide solution. The layers were separated, and the aqueous phase was extracted with ethyl acetate (3×50 mL). The combined organic layers were washed with brine, dried over potassium carbonate, filtered, and concentrated to give the crude product. Purification by column chromatography on silica gel (elution with 5% ethyl acetate-hexanes ) provided 2.5 g (86%) of product as colorless oil. $^1$H NMR (CDCl$_3$): δ 1.38 (s, 3H), 1.58–1.70 (m, 1H), 1.75–1.99 (m, 2H), 2.18–2.26 (m, 1H), 2.70–2.89 (m, 2H), 4.65 (ABq, J=11.6, 15.2 Hz, 2H), 5.34 (s, 2H), 5.39 (br s, 1H), 6.60 (d, J=8.5 Hz, 1H), 7.24–7.40 (m, 8H), 7.46 (d, J=7.1 Hz, 2H), 7.72 (d, J=8.5 Hz, 1H), $^{13}$C NMR (CDCl$_3$): δ 19.33, 26.47, 33.02, 33.45, 58.41, 67.40, 77.08, 108.48, 127.67, 128.02, 128.11, 128.27, 128.33, 128.36, 137.61, 137.99, 138.41, 155.10, 161.69. CIMS (NH$_3$) m/e 375 (M+1), 252.

(e) Preparation of 2-Benzyloxy-5,6,7,8-tetrahydro-5-methyl-2-5-quinolinamine (12) (Formula IV: Q=—CH$_2$—; R$^1$=H: —W—X—=—N=C(OR$^3$)—; R$^3$=benzyl: 5-CH$_3$ Substituted)

Borane-tetrahydrofuran (20 mL, 20 mmol, 1.0 M solution in tetrahydrofuran was added dropwise to a 0° C. solution of compound 11 (2.5 g, 6.7 mmol) prepared as described in (d) above in 10 mL of tetrahydrofuran. The mixture was then heated at reflux for 2 hours. Subsequently the mixture was cooled to 0° C., and 4 mL of water was carefully added. The tetrahydrofuran was removed in vacuo, 7 mL of 20% aqueous potassium hydroxide was added, and the resulting mixture was heated at reflux for 1.5 hours. The mixture was allowed to cool to room temperature, and the product was extracted into dichloromethane. The combined organic layers were washed with brine, dried over potassium carbonate, filtered, and concentrated to give crude product. Purification on silica gel (elution with ethyl acetate-methanol 2:1) provided 0.8 g (44%) of product as colorless oil. $^1$H NMR (CDCl$_3$): δ 1.40 (s, 3H), 1.62 (s, 2H), 1.70–1.96 (m, 4H), 2.72–2.90 (m, 2H), 5.34 (s, 2H), 6.63 (d, J=8.5 Hz, 1H), 7.26–7.39 (m, 3H), 7.46 (d, J=7.1 Hz, 2H), 7.73 (d, J=8.5 Hz, 1H). $^{13}$C NMR (CDCl$_3$): δ 19.82, 31.48, 32.94, 40.89, 50.50, 67.37, 108.90, 127.66, 128.08, 128.34, 132.53, 137.38, 137.63, 153.14, 161.36. CIMS(NH$_3$) m/e: 269 (M+1), 252.

(f) Preparation of rac-/meso-N,N'-di-5'-(5',6',7',8'-Tetrahydro-2'-benzyloxy-5'-methylquinolinyl)-1,10-diaminodecane (rac-/meso-18 g)

Compound 12 (537 mg, 2 mmol) prepared as described in (e) above sebacic dialdehyde (170 mg, 1 mmol) prepared as described in (a) above and 8 drops of acetic acid in benzene (50 mL) was refluxed with azeotropic removal of water for 24 hours. The resulting solution was cooled, the solvent was removed in vacuo, and the residue oil was reduced without further purification.

Sodium borohydride (151 mg, 4 mmol) was added to a solution of the crude imine in 50 mL of methanol, and the resulting mixture was stirred at room temperature for 12 hours. The solvent was removed in vacuo, the residue was quenched with water, and then the product was extracted into dichloromethane (3×30 mL). The combined organic layers were washed with brine, dried over MgSO$_4$ and filtered, and then concentrated to give an oily crude product. The crude product was purified by column separation, eluting with ethyl acetate-methanol (3:1) to give the pure o-benzyl dimer 324 mg (48%) as colorless oil. $^1$HNMR (CDCl$_3$): δ 1.15–1.48 (m, 22H), 1.48–1.68 (m, 4H), 1.78–2.07 (m, 6H), 2.12–2.20 (m, 2H), 2.41–2.50 (m, 2H), 2.78 (t, J=6.3 Hz, 4H), 5.33 (ABq, J=12.3, 15.5 Hz, 4H), 6.61 (d, J=8.5 Hz, 2H), 7.27–7.38 (m, 6H), 7.46 (d, J=7.1 Hz, 4H), 7.62 (d, J=8.5 Hz, 2H). $^{13}$C NMR (CDCl$_3$): δ 19.99, 27.36, 29.44, 29.47, 30.68, 30.92, 32.86, 34.21, 42.37, 54.52, 67.35, 108.65, 127.62, 128.05, 128.31, 130.73, 137.54, 137.62, 154.41, 161.25. CIMS (NH$_3$): m/e 675 (M+1), 503, 424, 252.

EXAMPLE 7

Preparation of rac-/meso-N,N'-di-5'-(5',6',7',8'-Tetrahydro-5'-methylquinolinonyl)-1,10-diaminodecane, Fumaric Acid Salt (rac-/meso-19 g.1.5 Fumaric Acid) (Formula IA: Q=—CH$_2$—; R$^1$=H,: —W—X—=—N(R$^2$)—C(O)—; R$^2$=H; m=1; R$^4$=5-CH$_3$; Divalent Linking Group=—(CH$_2$)$_n$—; n=10)

A mixture of compound 18 g (270 mg, 0.4 mmol) prepared as described in Example 6 above and 130 mg of 10% palladium on carbon in 10 mL of absolute ethanol was stirred under a H$_2$-filled balloon at room temperature for 48 hours. The catalyst was removed by filtration, and the filtrate was concentrated to afford a crude product. Purification by preparative silica gel plate (elution with dichloromethane-methanol 1:1) to afford 60 mg (30%) of free amine 19 g as a colorless oil. $^1$H NMR (CDCl$_3$): δ 1.23 (s, 14), 1.28 (s, 6H), 1.32–1.45 (m, 4H), 1.50–1.60 (m, 2H), 1.72–2.04 (m, 6H), 2.12–2.22 (m, 2H), 2.42–2.50 (m, 2H), 2.68 (t, J=5.9 Hz, 4H), 6.42 (d, J=9.4 Hz, 2H), 7.57 (d, J=9.4 Hz, 2H). $^{13}$C NMR (CDCl$_3$): δ 19.05, 27.25, 27.32, 29.42, 29.63, 30.88, 33.74, 42.27, 53.09, 53.28, 117.18, 120.75, 140.96, 143.91, 164.84. CIMS (NH$_3$): m/e 495 (M+1), 472, 334, 323, 173, 162.

50 mg (0.1 mmol) free amine was dissolved in minimum methanol, and 23 mg (0.2 mmol) of fumaric acid in minimum methanol was added to above solution. After several days standing at room temperature, 50 mg (68% based on free amine) of the desired fumarate salt of 19 g was obtained. m.p. 147.5–149° C. $^1$H NMR (D$_2$O): δ 1.15–1.38 (m, 12H), 1.54–1.66 (m, 4H), 1.68 (s, 6H), 1.83–2.06 (m, 6H), 2.08–2.20 (m, 2H), 2.63–2.84 (m, 6H), 2.92–3.02 (m, 2H), 6.56 (d, J=9.5 Hz, 2H), 6.60 (s, 3H), 7.79 (d, J=9.5 Hz, 2H). $^{13}$C NMR (CD$_3$OD): δ 18.51, 26.31, 27.26, 27.47, 27.72, 29.53, 29.80, 32.62, 43.66, 115.91, 118.91, 136.54, 142.07, 148.90, 165.78, 174.16. HPLC (area%): 21.2 min. 90.9%. Analysis: Calcd. for C$_{30}$H$_{46}$N$_4$O$_2$.1.5C$_4$H$_4$O$_4$.3.5H$_2$O: C, 59.08; H, 8.13; N, 7.66. Found: C, 58.93; H, 7.99; N, 7.51.

EXAMPLE 8

Preparation of (S,S)-(−)-N,N'-di-5'-(5',6',7',8'-Tetrahydroquinolin-2-onyl)-1,12-diaminododecane, bis-Hydrochloride Salt [(S,S)-(−)-13i.2HCl]
(Formula IA: Q=—CH$_2$—; R$^1$=H; —W—X—=—N(R$^2$)—C(O)—; R$^2$=H: m=0: Divalent Linking Group=—(CH$_2$)$_n$—; n=12)

(a) Preparation of (±)-2-Benzyloxy-5,6,7,8-tetrahydro-5-quinolinamine [(±)-21] (Formula IV: Q=—CH$_2$—; R$^1$=H: —W—X—=—N=C(OR$^3$)—; R$^3$=Benzyl: Unsubstituted)

A solution of compound 9 (11.4 g, 45 mmol) prepared as described in Example 6(b) above and O-benzylhydroxylamine hydrochloride (7.9 g, 49.5 mmol) in 100 mL of pyridine was stirred at room temperature for 16 hours. The solvent was removed in vacuo and dichloromethane (200 mL) was added to the residue. The dichloromethane solution was washed with 10% sodium bicarbonate solution (2×30 mL) and water (2×30 mL). The organic solution was dried (MgSO$_4$), filtered, concentrated, and purified by column chromatography (elution with hexanes-ethyl acetate 4:1) to afford 15.3 g (95%) of a 10:1 mixture of oxime ether isomers 20. Isomer A (major): colorless oil, $^1$H NMR (CDCl$_3$): δ 1.88 (quin, J=6.4 Hz, 2H), 2.76 (t, J=6.6 Hz, 2H), 2.81 (t, J=6.2 Hz, 2H), 5.18 (s, 2H), 5.37 (s, 2H), 6.62 (d, J=8.4 Hz, 1H), 7.29–7.46 (m, 5H), 8.15 (d, J=8.4 Hz, 1H). $^{13}$C NMR (CDCl$_3$): δ 20.84, 23.74, 32.21, 67.62, 76.13, 109.48, 119.92, 127.69, 127.79, 128.08, 128.29, 128.38, 135.12, 137.21, 138.07, 153.34, 156.67, 163.20. CIMS (NH$_3$) m/e: 359 (M+1, 100), 358 (M$^+$, 70), 251 (12), 91 (12). Isomer B (minor): m.p. 73–74.5° C.; $^1$H NMR (CDCl$_3$): δ 1.95–2.04 (m, 2H), 2.50–2.54 (m, 2H), 2.93 (t, J=6.4 Hz, 2H), 5.16 (s, 2H), 5.37 (s, 2H), 6.59 (d, J=8.7 Hz, 1H), 7.28–7.45 (m, 5H), 8.79 (d, J=8.7 Hz, 1H). $^{13}$C NMR (CDCl$_3$): δ 22.26, 31.31, 33.29, 67.54, 76.38, 108.11, 118.27, 127.68, 127.81, 127.85, 128.09, 128.34, 128.36, 137.12, 137.86, 141.77, 150.59, 158.72, 162.58. CIMS (NH$_3$) m/e: 359 (M+1, 100), 358 (M$^+$, 70), 251 (12), 91 (12). Analysis: Calcd. for C$_{23}$H$_{22}$N$_2$O$_2$: C, 77.07; H, 6.19; N, 7.82. Found: C, 77.27; H, 6.22; N, 7.92.

Borane-tetrahydrofuran (134 mL, 134 mmol, 1.0 M solution in THF) was added dropwise to a 0° C. solution of the oxime ether isomers 20 (16.0 g, 44.6 mmol) in 20 mL of THF. The mixture was stirred at room temperature for 12 hours and then heated at reflux for 2 hours. Subsequently the mixture was cooled to 0° C., and 30 mL of water was carefully added. The tetrahydrofuran was removed in vacuo, 45 mL of 20% aqueous potassium hydroxide was added, and the resulting mixture was heated at reflux for 1.5 hours. The mixture was allowed to cool to room temperature, and the product was extracted into dichloromethane. The combined organic layers were washed with brine, dried over potassium carbonate, filtered, concentrated, and purified by column chromatography (elution with methanol) to afford 7.5 g (66%) of (±)-21 as a colorless oil. $^1$H NMR (CDCl$_3$): δ 1.53 (s, br, 2H), 1.59–1.68 (m, 1H), 1.74–1.86 (m, 1H), 1.92–2.06 (m, 2H), 2.70–2.90 (m, 2H), 3.92 (t, J=4.3 Hz, 2H), 6.62 (d, J=8.4 Hz, 1H), 7.27–7.47 (m, 5H), 7.61 (d, J=8.4 Hz, 1H). $^{13}$C NMR (CDCl$_3$): δ 19.17, 32.40, 33.76, 48.58, 67.39, 108.63, 127.66, 128.06, 128.34, 128.74, 137.60, 139.07, 154.09, 161.69. CIMS (CH$_4$): m/e 255 (M+1, 100), 238 (35). Analysis: Calcd. for C$_{16}$H$_{18}$N$_2$O.0.2H$_2$O: C, 74.51; H, 7.19; N, 10.86. Found: C, 74.31; H, 7.32; N, 10.99.

(b) Preparation of (S)-(+)-2-Benzyloxy-5,6,7,8-tetrahydro-5-quinolinamine [(S)-(+)-21]

(±)-21 (7.0 g, 27.5 mmol) prepared as described in (a) above and (R)-(−)-mandelic acid (4.2 g, 27.6 mmol) were dissolved in. 250 mL of methanol. After standing overnight, white crystals (4.4 g) were obtained by filtration; a second crystallization from 200 mL of methanol afforded the n salt [(R)-(−)-mandelic acid salt of (+)-21] (3.2 g, 29%) of fine crystals. mp 187–188° C. [α]$^{20}$$_D$=−61.6° (c=1, MeOH). $^1$H NMR (CD$_3$OD): δ 1.85–2.15 (m, 4H), 2.70–2.92 (m, 2H), 4.41 (t, J=4.8 Hz, 2H), 4.85 (s, 1H), 5.34 (q, J=12.4, 16.3 Hz, 2H), 6.70 (d, J=8.4 Hz, 1H), 7.27–7.47 (m, 5H), 7.66 (d, J=8.4 Hz, 1H). $^{13}$C NMR (CD$_3$OD): δ 19.36, 28.99, 32.93, 49.71, 69.04, 76.41, 110.43, 122.09, 128.22, 128.55, 129.13, 129.33, 129.68, 139.01, 141.12, 143.72, 157.43, 164.68, 179.59.

Single crystal x-ray diffraction of the n salt revealed that the (+)-21 possesses the (S)-configuration (colorless needles, data collection at 293 (2) ° K; monoclinic; P2 (1) space group; unit cell dimensions a=9.580 (3) Å, b=5.972 (2) Å, c=17.834 (6) Å, β=99.18 (2)°; Z=2, R1=0.0835, wR2=0.1998, GOF=1.000).

The (R)-(−)-mandelic acid salt of (S)-(+)-21 (3.2 g) was stirred with 2 N sodium hydroxide (20 mL) at 50° C. for 10 minutes. The solution was extracted with dichloromethane (3×30 mL), the combined organic layer washed with water (20 mL), dried (MgSO$_4$), and concentrated in vacuo to afford (S)-(+)-21 (2.0 g, 29% yield based on racemic amine) as colorless oil. [α]$^{20}$$_D$=+4.9° (c=1, MeOH). $^1$H NMR (CDCl$_3$): δ 1.54 (s, br, 2H), 1.59–1.68 (m, 1H), 1.73–1.86 (m, 1H), 1.92–2.06 (m, 2H), 2.70–2.90 (m, 2H), 3.92 (t, J=4.3, 6.0 Hz, 2H), 5.34 (s, 2H), 6.62 (d, J=8.4 Hz, 1H), 7.27–7.47 (m, 5H), 7.61 (d, J=8.4 Hz, 1H). $^{13}$C NMR (CDCl$_3$): δ 19.17, 32.39, 33.79, 48.58, 67.36, 108.61, 127.62, 128.02, 128.31, 128.74, 137.65, 139.02, 154.08, 161.70. CIMS (CH$_4$): m/e 255 (M+1, 100), 238 (35).

(c) Preparation of (S,S)-(−)-N,N'-di-5'-(5',6',7',8'-Tetrahydro-2-'-benzyloxyquinolinyl)-1,10-decanedicarboxamide (S,S)-(−)-22i (S)-(+)-21 (250 mg, 1 mmol) prepared as described in (b) above, triethylamine (100 mg, 1 mmol) and anhydrous benzene (15 mL) was stirred under nitrogen at room temperature, dodecanedioyl dichloride (134 mg, 0.5 mmol) in benzene (3 mL) was added dropwise to the above solution by syringe. The reaction mixture was then refluxed for 4 hours. Then the mixture was cooled and the solvent was removed in vacuo. The residue was dissolved in dichloromethane (50 mL), washed with water (3×20 mL). The organic phase was dried and the solvent was concentrated to give the solid, it was recrystallized from dichloromethane-ethyl acetate to afford (S,S)-(−)-N,N'-di-5'-(5',6',7',8'-tetrahydro-2-'-benzyloxyquinolinyl)-1,10-decanedicarboxamide (S,S)-(−)-22i (320 mg, 91%). m.p. 175–177° C. [α]$^{20}$$_D$=91.5° (c=1, CHCl$_3$). $^1$H NMR (CDCl$_3$): δ 1.27 (s, 12H), 1.63 (quin, J=6.9 Hz, 4H), 1.70–1.82 (m, 2H), 1.87 (quin, J=5.9 Hz, 4H), 1.93–2.05 (m, 2H), 2.16 (t, J=7.6 Hz, 4H), 2.70–2.89 (m, 4H), 5.08–5.17 (m, 2H), 5.33 (s, 4H), 5.71 (d, J=8.6 Hz, 2H), 6.59 (d, J=8.5 Hz, 2H), 7.26–7.46 (m, 12H). $^{13}$C NMR (CDCl$_3$): δ 19.64, 25.76, 29.17, 29.27, 29.91, 32.11, 36.93, 46.32, 67.46, 109.11, 124.99, 127.72, 128.06, 128.36, 137.50, 139.51, 154.78, 162.12, 172.41. CIMS (CH$_4$): m/e 703 (M+1, 22), 611 (15), 255 (30), 238 (100), 107 (30). Analysis: Calcd. for C$_{44}$H$_{54}$N$_4$O$_4$: C, 75.18; H, 7.74; N, 7.97. Found: C, 75.07; H, 7.84; N, 8.04.

(d) Preparation of (S,S)-(–)-N,N'-di-5'-(5',6',7',8'-Tetrahydro-2'-benzyloxyquinolinyl)-1,12-diaminododecane (S,S)-(–)-23i (Formula IA: Q=—CH$_2$—; R$^1$=H; —W—X—=—N=C(OR$^3$)—; R$^3$=benzyl: m=0: Divalent Linking Group=—(H H$_2$)$_n$—; n=12)

Borane-tetrahydrofuran (2.4 mL, 2.4 mmol, 1.0 M solution in tetrahydrofuran) was added dropwise to a 0° C. solution of (S,S)-(–)-22i (281 mg, 0.4 mmol) prepared as described in (c) above in 2 mL of tetrahydrofuran. The mixture was heated at reflux for 4 hours. Subsequently the mixture was cooled to 0° C., and 1 mL of water was carefully added. The tetrahydrofuran was removed in vacuo, 1 mL of 20% aqueous potassium hydroxide was added, and the resulting mixture was heated at reflux for 2 hours. The mixture was allowed to cool to room temperature, and the product was extracted into dichloromethane. The combined organic layers were washed with brine, dried over potassium carbonate, filtered, and concentrated to give crude oil. Purification by column chromatography on silica gel (elution with dichloromethane-methanol 10:1) to afford (S,S)-(–)-N,N'-di-5'-(5',6',7',8'-tetrahydro-2'-benzyloxyquinolinyl)-1,12-diaminododecane (S,S)-(–)-23i (235 mg, 87%). mp 52–54° C. [α]$^{20}$$_D$=–24.2° (c=1, CHCl$_3$). $^1$H NMR (CDCl$_3$): δ 1.26 (s, 18H), 1.48 (quin, J=6.6 Hz, 4H), 1.70–1.89 (m, 6H), 1.90–2.05 (m, 2H), 2.56–2.89 (m, 8H), 3.69 (t, J=4.6 Hz, 2H), 6.59 (d, J=8.4 Hz, 2H), 7.26–7.47 (m, 10H), 7.56 (d, J=8.4 Hz, 2H). $^{13}$C NMR (CDCl$_3$): δ 18.84, 27.42, 28.25, 29.58, 30.59, 32.34, 47.12, 54.59, 67.35, 108.31, 127.46, 127.61, 128.04, 128.31, 137.74, 139.66, 154.64, 161.76. CIMS (NH$_3$): m/e 675 (M+1, 18), 436 (20), 238 (100). Analysis: Calcd. for C$_{44}$H$_{58}$N$_4$O$_2$: C, 78.30; H, 8.66; N, 8.30. Found: C, 77.89; H, 8.82; N, 8.40.

(e) Preparation of (S,S)-(–)-N,N'-di-5'-(5',6',7',8'-Tetrahydroquinolin-2-onyl)-1,12-diaminododecane, bis-Hydrochloride Salt [(S,S)-(–)-13i.2HCl]

A mixture of (S,S)-(–)-23i (202 mg, 0.3 mmol) pepared as described in (d) above and 150 mg of 10% palladium on carbon in 50 mL of absolute ethanol was stirred under a hydrogen-filled balloon at room temperature for 24 hours. The catalyst was removed by filtration, washed with 20 mL of methanol-chloroform (1:1). The filtrate was concentrated to afford pale solid, it was crystallized from chlorommethanol to afford pure (S,S)-(–)-13i (135 mg, 91%), mp 193–195° C., [α]$^{20}$$_D$=–40.5° (c=0.4, MeOH-CHCl$_3$ 1:1). The above amine was dissolved in methanolic HCl methanol, the solution was concentrated and then ethanol was added to it. After standing at room temperature for several days, (S,S)-(–)-13i hydrochloride salt was obtained. m p. 169–170° C. [α]$^{20}$$_D$=–47.5° (c=1, MeOH). $^1$H NMR (D$_2$O): δ 1.20–1.43 (m, 16H), 1.69 (quin, J=7.4 Hz, 4H), 1.82–2.10 (m, 6H), 2.15–2.26 (m, 2H), 2.68–2.85 (m, 4H), 3.00–3.18 (m, 4H), 4.38 (s, 2H), 6.52 (d, J=9.3 Hz, 2H), 7.69 (d, J=9.3 Hz, 2H); $^{13}$C NMR (CD$_3$OD): δ 17.32, 25.19, 27.60, 27.97, 30.47, 30.70, 30.81, 47.32, 55.01, 113.71, 119.07, 149.41, 152.03, 163.65; MS (NH$_3$): m/e 495 (M+1), 295, 201, 165, 148. HPLC (area%): 19.1 min. 94.6% Analysis: Calcd. for C$_{30}$H$_{46}$N$_4$O$_2$.2HCl.2.5H$_2$O: C, 58.81; H, 8.72; N, 9.14; Cl, 11.57. Found: C, 58.84; H, 8.87; N, 9.18; Cl 11.34.

Further dimeric compounds of the invention were prepared by processes similar to those described in Examples 1 to 8 above and broadly as set out in the following reaction schemes. Details of these compounds are set out in Table I below. In this table, the compounds are identified by reference to formula IA and the compound numbers provided in the reaction schemes. Characterising data for these compounds is provided in Table IA below. All dimeric compounds of the invention listed in Table I are homodimers.

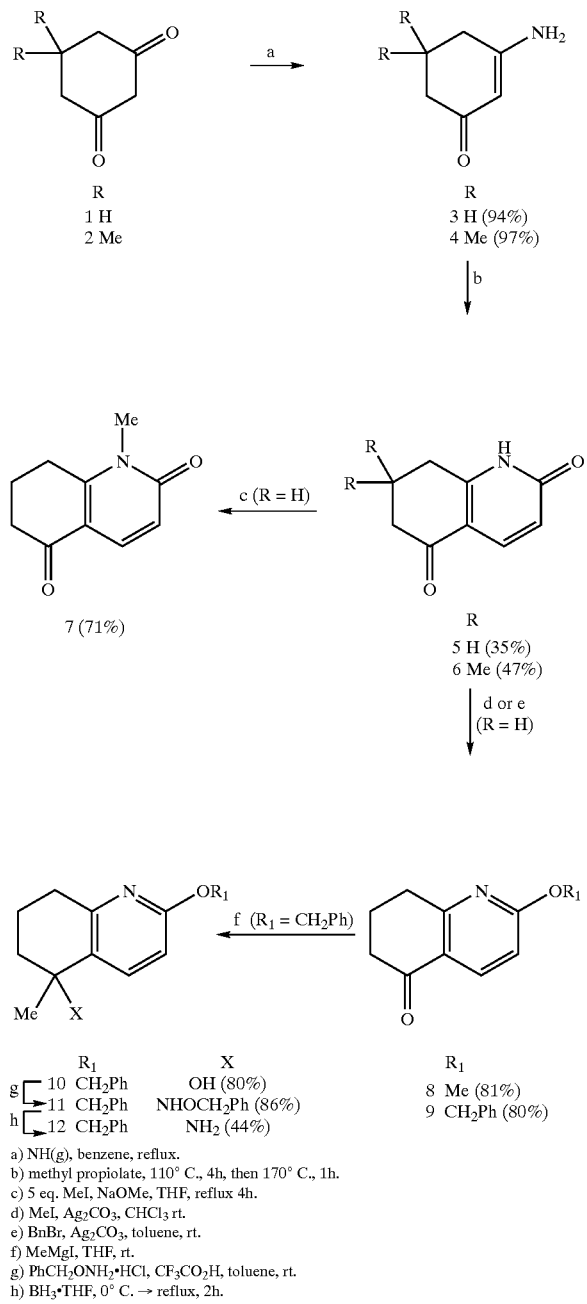

Reaction Scheme 1 a) NH(g), benzene, reflux.
b) methyl propiolate, 110° C., 4h, then 170° C., 1h.
c) 5 eq. MeI, NaOMe, THF, reflux 4h.
d) MeI, Ag$_2$CO$_3$, CHCl$_3$ rt.
e) BnBr, Ag$_2$CO$_3$, toluene, rt.
f) MeMgI, THF, rt.
g) PhCH$_2$ONH$_2$•HCl, CF$_3$CO$_2$H, toluene, rt.
h) BH$_3$•THF, 0° C. → reflux, 2h.

Reaction Scheme 2
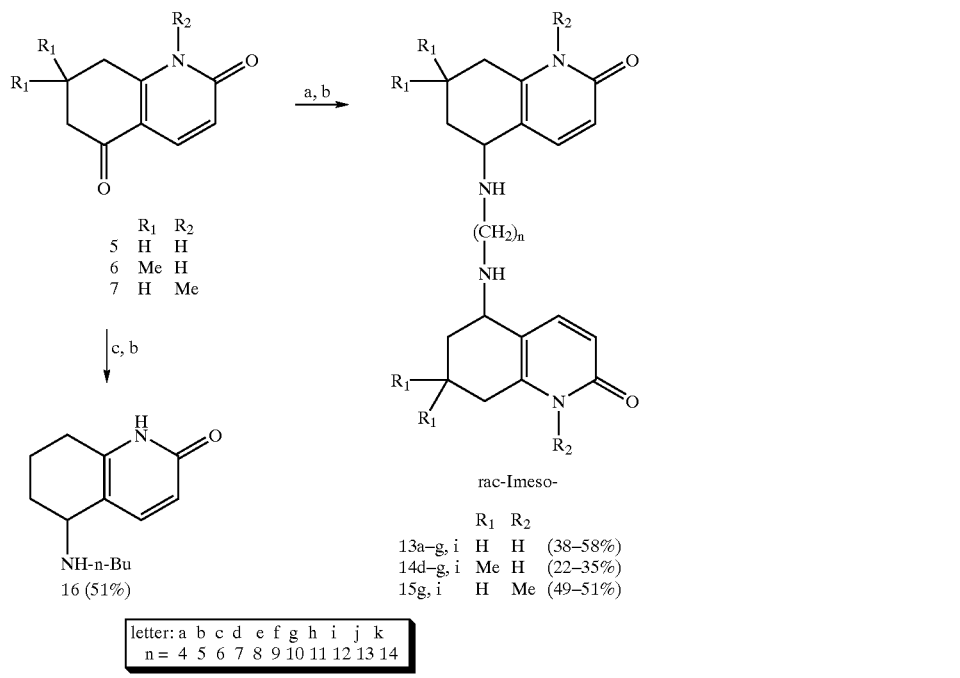
| letter: | a | b | c | d | e | f | g | h | i | j | k |
|---|---|---|---|---|---|---|---|---|---|---|---|
| n = | 4 | 5 | 6 | 7 | 8 | 9 | 10 | 11 | 12 | 13 | 14 |
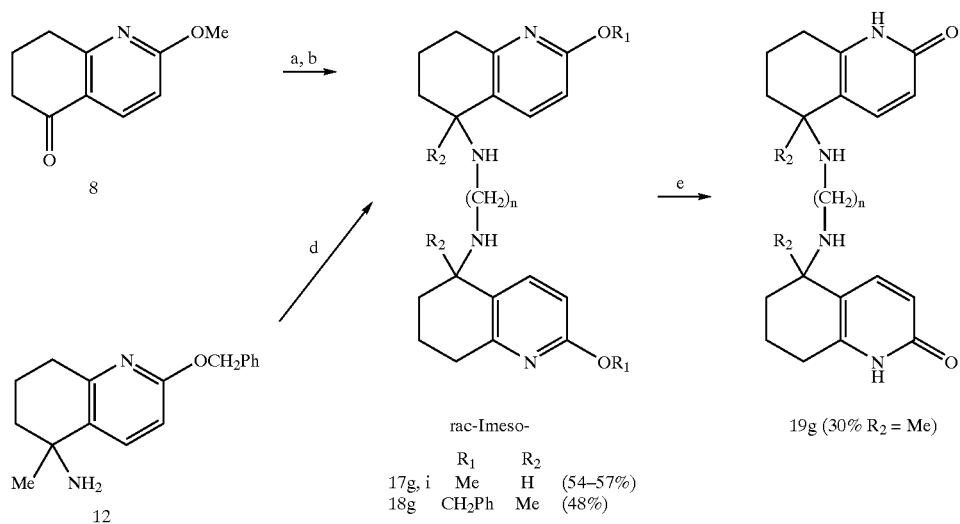
a) 0.5 eq. $H_2N(CH_2)_nNH_2$, cat acetic acid, benzene, reflux 24h
b) $NaBH_4$, MeOH, 12h
c) 1.0 eq. n-$BuNH_2$, cat. acetic acid, reflux 24h
d) 0.5 eq. OHC—$(CH_2)_8$—CHO, cat. acetic acid benzene, reflux 24h
e) $H_2$, 10% Pd/C, ethanol, 48h
Reaction Scheme 3
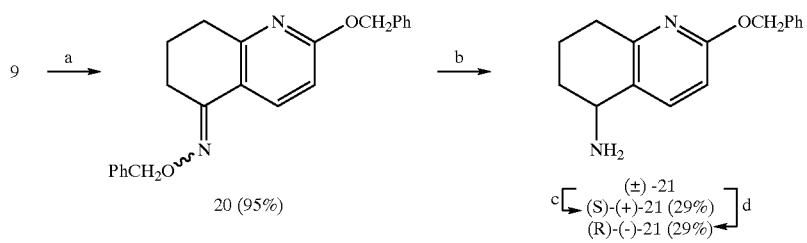

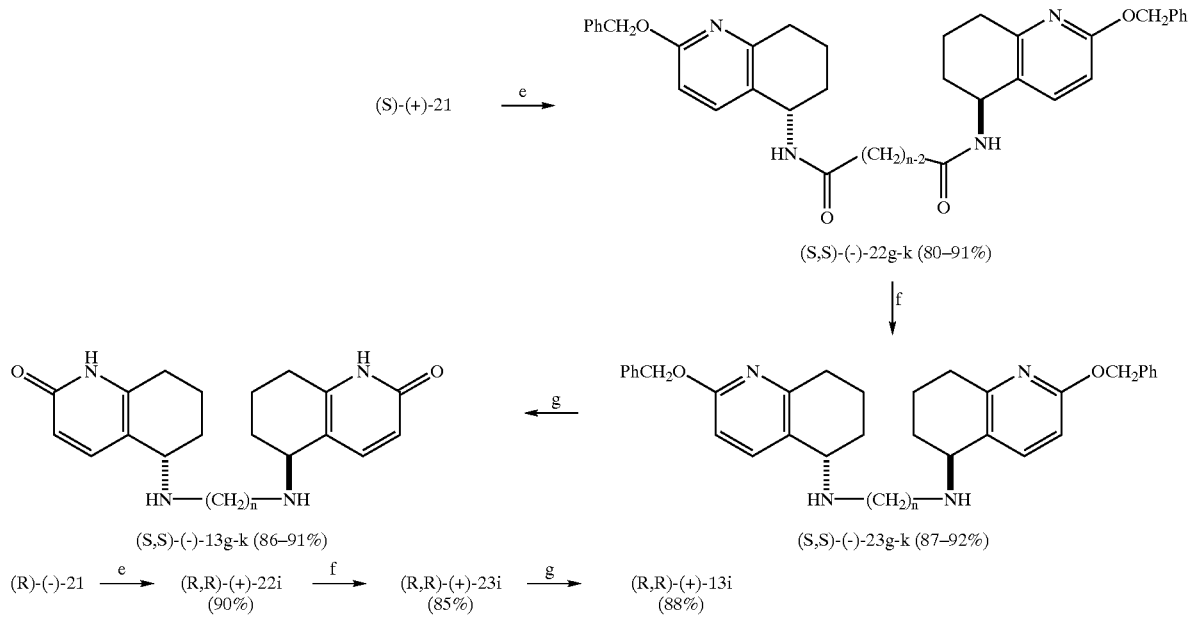

(S)-(+)-21 →[e]

(S,S)-(-)-22g-k (80–91%)

↓ f (S,S)-(-)-13g-k (86–91%) ←[g] (S,S)-(-)-23g-k (87–92%)

(R)-(-)-21 →[e] (R,R)-(+)-22i →[f] (R,R)-(+)-23i →[g] (R,R)-(+)-13i
            (90%)           (85%)              (88%)

a) $PhCH_2ONH_2 \cdot HCl$, pyridine, rt. 10h
b) $BH_3 \cdot THF$ rt 12h, reflux 2h
c) (R)-(-)-mandelic acid, ethanol, 2 recrystallizations; $CH_2Cl_2$ 10% NaOH
d) as in c) but use (S)-(+)-mandelic acid
e) 0.5 equiv. $ClC(O)\text{—}(CH_2)_{n-2}C(O)Cl$, $Et_3N$, benzene, reflux 4h
f) 6 equiv. $BH_3 \cdot THF$, rt 12h, reflux 2h; 20% KOH, reflux 15h
g) $H_2$, 10% Pd/C, EtOH, 24h.

TABLE I (NB In all compounds, Q = —$CH_2$— and $R^1$ = H)

| Compound No. | Isomer | —W—X— | $R^2$ | $R^3$ | m | $R^4$ | Divalent linking group |
|---|---|---|---|---|---|---|---|
| 13a. 3HCl | rac-/meso- | —N($R^2$)—C(O)— | —H | — | 0 | — | —$(CH_2)_4$— |
| 13b | rac-/meso- | —N($R^2$)—C(O)— | —H | — | 0 | — | —$(CH_2)_5$— |
| 13b. 3HCl | rac-/meso- | —N($R^2$)—C(O)— | —H | — | 0 | — | —$(CH_2)_5$— |
| 13c | rac-/meso- | —N($R^2$)—C(O)— | —H | — | 0 | — | —$(CH_2)_6$— |
| 13c. 2.9HCl | rac-/meso- | —N($R^2$)—C(O)— | —H | — | 0 | — | —$(CH_2)_6$— |
| 13e | rac-/meso- | —N($R^2$)—C(O)— | —H | — | 0 | — | —$(CH_2)_8$— |
| 13e. 2HCl | rac-/meso- | —N($R^2$)—C(O)— | —H | — | 0 | — | —$(CH_2)_8$— |
| 13f | rac-/meso- | —N($R^2$)—C(O)— | —H | — | 0 | — | —$(CH_2)_9$— |
| 13f. 2HCl | rac-/meso- | —N($R^2$)—C(O)— | —H | — | 0 | — | —$(CH_2)_9$— |
| 13g | rac-/meso- | —N($R^2$)—C(O)— | —H | — | 0 | — | —$(CH_2)_{10}$— |
| 13g. 2HCl | rac-/meso- | —N($R^2$)—C(O)— | —H | — | 0 | — | —$(CH_2)_{10}$— |
| 13i | rac-/meso- | —N($R^2$)—C(O)— | —H | — | 0 | — | —$(CH_2)_{12}$— |
| 13i. 2HCl | rac-/meso- | —N($R^2$)—C(O)— | —H | — | 0 | — | —$(CH_2)_{12}$— |
| 14e | rac-/meso- | —N($R^2$)—C(O)— | —H | — | 2 | 7,7-$(CH_3)_2$ | —$(CH_2)_8$— |
| 14e. 2 fumaric acid | rac-/meso- | —N($R^2$)—C(O)— | —H | — | 2 | 7,7-$(CH_3)_2$ | —$(CH_2)_8$— |
| 14f. | rac-/meso- | —N($R^2$)—C(O)— | —H | — | 2 | 7,7-$(CH_3)_2$ | —$(CH_2)_9$— |
| 14f. 2 fumaric acid | rac-/meso- | —N($R^2$)—C(O)— | —H | — | 2 | 7,7-$(CH_3)_2$ | —$(CH_2)_9$— |
| 14g | rac-/meso- | —N($R^2$)—C(O)— | —H | — | 2 | 7,7-$(CH_3)_2$ | —$(CH_2)_{10}$— |
| 14g. 2 fumaric acid | rac-/meso- | —N($R^2$)—C(O)— | —H | — | 2 | 7,7-$(CH_3)_2$ | —$(CH_2)_{10}$— |
| 14i. | rac-/meso- | —N($R^2$)—C(O)— | —H | — | 2 | 7,7-$(CH_3)_2$ | —$(CH_2)_{12}$— |
| 14i. 2 fumaric acid | rac-/meso- | —N($R^2$)—C(O)— | —H | — | 2 | 7,7-$(CH_3)_2$ | —$(CH_2)_{12}$— |
| 15i | rac-/meso- | —N($R^2$)—C(O)— | —$CH_3$ | — | 0 | — | —$(CH_2)_{12}$— |
| 15i. 2 fumaric acid | rac-/meso- | —N($R^2$)—C(O)— | —$CH_3$ | — | 0 | — | —$(CH_2)_{12}$— |
| 17i | rac-/meso- | —N=C(O$R^3$)— | — | —$CH_3$ | 0 | — | —$(CH_2)_{12}$— |
| 17i. 2 fumaric acid | rac-/meso- | —N=C(O$R^3$)— | — | —$CH_3$ | 0 | — | —$(CH_2)_{12}$— |
| 22g | (S,S)-(-)- | —N=C(O$R^3$)— | — | benzyl | 0 | — | —C(O)—$(CH_2)_8$—C(O)— |
| 23g | (S,S)-(-)- | —N=C(O$R^3$)— | — | benzyl | 0 | — | —$(CH_2)_{10}$— |
| 13g | (S,S)-(-)- | —N($R^2$)—C(O)— | —H | — | 0 | — | —$(CH_2)_{10}$— |
| 13g. 2HCl | (S,S)-(-)- | —N($R^2$)—C(O)— | —H | — | 0 | — | —$(CH_2)_{10}$— |
| 22h | (S,S)-(-)- | —N=C(O$R^3$)— | — | benzyl | 0 | — | —C(O)—$(CH_2)_9$—C(O)— |
| 23h | (S,S)-(-)- | —N=C(O$R^3$)— | — | benzyl | 0 | — | —$(CH_2)_{11}$— |
| 13h | (S,S)-(-)- | —N($R^2$)—C(O)— | —H | — | 0 | — | —$(CH_2)_{11}$— |
| 13.h. 2HCl | (S,S)-(-)- | —N($R^2$)—C(O)— | —H | — | 0 | — | —$(CH_2)_{11}$— |
| 22j | (S,S)-(-)- | —N=C(O$R^3$)— | — | benzyl | 0 | — | —C(O)—$(CH_2)_{11}$—C(O)— |
| 23j | (S,S)-(-)- | —N=C(O$R^3$)— | — | benzyl | 0 | — | —$(CH_2)_{13}$— |
| 13j | (S,S)-(-)- | —N($R^2$)—C(O)— | —H | — | 0 | — | —$(CH_2)_{13}$— |

TABLE I-continued (NB In all compounds, Q = —CH$_2$— and R$^1$ = H)

| Compound No. | Isomer | —W—X— | R$^2$ | R$^3$ | m | R$^4$ | Divalent linking group |
|---|---|---|---|---|---|---|---|
| 13j. 2HCl | (S,S)-(−)- | —N(R$^2$)—C(O)— | —H | — | 0 | — | —(CH$_2$)$_{13}$— |
| 22k | (S,S)-(−)- | —N=C(OR$^3$)— | — | benzyl | 0 | — | —C(O)—(CH$_2$)$_{12}$—C(O)— |
| 23k | (S,S)-(−)- | —N=C(OR$^3$)— | — | benzyl | 0 | — | —(CH$_2$)$_{14}$— |
| 13k | (S,S)-(−)- | —N(R$^2$)—C(O)— | —H | — | 0 | — | —(CH$_2$)$_{14}$— |
| 13k. 2HCl | (S,S)-(−)- | —N(R$^2$)—C(O)— | —H | — | 0 | — | —(CH$_2$)$_{14}$— |
| 22i | (R,R)-(+) | —N=C(OR$^3$)— | — | benzyl | 0 | — | —C(O)—(CH$_2$)$_{10}$—C(O)— |
| 23i | (R,R)-(+) | —N=C(OR$^3$)— | — | benzyl | 0 | — | —(CH$_2$)$_{12}$— |
| 13i | (R,R)-(+) | —N(R$^2$)—C(O)— | —H | — | 0 | — | —(CH$_2$)$_{12}$— |
| 13i. 2HCl | (R,R)-(+) | —N(R$^2$)—C(O)— | —H | — | 0 | — | —(CH$_2$)$_{12}$— |

TABLE IA

| Compound No./Isomer | Characterising Data |
|---|---|
| 13a. 3HCl rac-/meso- | m.p. 229–230 ° C. (Dec.) $^1$H NMR (D$_2$O): δ 1.83(s, br, 4H), 1.90–2.13 (m, 6H), 2.19–2.29(m, 2H), 2.70–2.85(m, 4H), 3.09–3.29(m, 4H), 4.42(s, br, 2H), 6.55(d, J = 9.4 Hz, 2H), 7.73 (d, J = 9.4 Hz, 2H); $^{13}$C NMR (CD$_3$OD): δ 17.12, 24.69, 25.42, 27.05, 46.26, 55.62, 111.68, 118.24, 145.53, 149.51, 166.15.CIMS (CH$_4$): m/e 383(M + 1), 295, 176, 148.HPLC (area %): 15.9 min. 99.8%. Analysis: Calcd. for C$_{22}$H$_{30}$N$_4$O$_2$ · 2.9HCl · H$_2$O: C, 52.20; H, 6.95; N, 11.07; Cl, 20.31. Found: C, 52.22; H, 7.05; N, 11.05; Cl, 19.90. |
| 13b rac-/meso- | mp 235–236 ° C. $^1$H NMR (CD$_3$OD): δ 1.35–1.48 (m, 2H), 1.48–1.60 (m, 4H), 1.68–1.73 (m, 4H), 1.73–2.00 (m, 4H), 2.48–2.69 (m, 8H), 3.62 (t, J = 4.8 Hz, 2H), 6.35 (d, J = 9.3 Hz, 2H), 7.59 (d, J = 9.3 Hz, 2H); $^{13}$C NMR (CD$_3$OD): δ 18.90, 26.82, 28.08, 28.47, 31.20, 48.04, 54.45, 118.05, 119.11, 145.60, 146.47, 166.13.CIMS (CH$_4$): m/e 397(M + 1), 295, 250, 176, 148, 103. |
| 13b. 3HCl rac-/meso- | mp 207–208 ° C (dec.). $^1$H NMR (CD$_3$OD): δ 1.48–1.61 (m, 2H), 1.82 (quin, J = 7.5 Hz, 4H), 1.92–2.10 (m, 6H), 2.18–2.32(m, 2H), 2.68–2.88(m, 4H), 3.02–3.20(m, 4H), 4.37(s, br, 2H), 6.54(d, J = 9.3 Hz, 2H), 7.80(d, J = 9.3 Hz, 2H); HPLC (area %): 4.6 min. 99.9%. Analysis: Calcd. for C$_{23}$H$_{32}$N$_4$O$_2$ · 3HCl · 1.5H$_2$O: C, 51.84; H, 7.19; N, 10.51; Cl, 19.96. Found: C, 51.50; H, 7.29; N, 10.47; Cl, 19.75. |
| 13c rac-/meso- | mp 218–220 ° C. $^1$H NMR (CD$_3$OD):. δ 1.32–1.42 (m, 4H), 1.45–1.60 (m, 4H), 1.68–1.84 (m, 4H), 1.84–2.00 (m; 4H), 3.61 (t, J = 4.8 Hz, 2H), 6.35 (d, J = 9.3 Hz, 2H), 7.59 (d, J = 9.3 Hz, 2H); $^{13}$C NMR (CD$_3$OD): δ 18.89, 28.07, 28.46, 28.94, 31.28, 48.09, 54.42, 118.03, 119.15, 145.59, 146.45, 166.12. FABMS: m/e 411(M + 1), 278, 264. |
| 13c. 2.9HCl rac-/meso- | mp 182–184 ° C (dec.). $^1$H NMR (D$_2$O): δ 1.41(s, 4H), 1.70 (apparent t, J = 6.5 Hz, 4H), 1.80–2.08 (m, 6H), 2.15–2.25 (m, 2H), 2.68–2.85 (m, 4H), 3.02–3.19 (m, 4H), 4.38 (s, 2H), 6.5 1 (d, J = 9.3 Hz, 2H), 7.67 (d, J = 9.3 Hz, 2H); HPLC (area %): 4.6 min. 98.9%. Analysis: Calcd. for C$_{24}$H$_{34}$N$_4$O$_2$ · 2.9HCl · 3H$_2$O: C, 50.54; H, 7.58; N, 9.82; Cl, 18.03. Found: C, 50.34; H, 7.33; N, 9.83; C1, 18.10. |
| 13e rac-/meso- | mp 215–216 ° C. $^1$H NMR (CD$_3$OD): δ 1.35 (s, 8H), 1.45–1.58 (m, 4H), 1.68–1.85 (m, 4H), 1.85–2.02 (m, 4H), 2.48–2.68 (m, 8H), 3.61(t, J = 4.9 Hz, 2H), 6.35(d, 9.3 Hz, 2H), 7.59(d, J = 9.3 Hz, 2H); $^{13}$C NMR (CD$_3$OD): δ 18.88, 28.07, 28.45, 28.97, 31.07, 31.30, 48.14, 54.43, 118.04, 119.11, 145.57, 146.46, 166.12;FABMS: m/e 439(M + 1), 370, 304. |
| 13e. 2HCl rac-/meso- | mp 202–203 ° C. (dec.) $^1$H NMR (D$_2$O): δ 1.34 (s, 8H), 1.69 (quin, J = 7.1 Hz, 4H), 1.80–2.08 (m, 6H), 2.15–2.25 (m, 2H), 2.68–2.85 (m, 4H), 3.00–3.18 (m, 4H), 4.37(t, J = 3.8 Hz, 2H), 6.5O(d, J = 9.3 Hz, 2H), 7.67(d, J = 9.3Hz, 2H); HPLC (area %): 18.2 min. 95.9%. Analysis: Calcd. for C$_{26}$H$_{38}$N$_4$O$_2$ · 2HCl · 1.5H$_2$O: C, 57.99; H, 8.05; N, 10.40. Found: C, 57.65; H, 8.09; N, 10.11. |
| 13f rac-/meso- | mp 218–219 ° C. $^1$H NMR (CD$_3$OD): δ 1.33 (s, 10H), 1.42–1.58 (m, 4H), 1.68–1.82 (m, 6H), 1.82–2.00 (m, |

TABLE IA-continued

| Compound No./Isomer | Characterising Data |
|---|---|
| | 2H), 2.48–2.68 (m, 8H), 3.61 (t, J = 4.7 Hz, 2H), 6.35 (d, J = 9.3 Hz, 2H), 7.59 (d, J = 9.3 Hz, 2H); $^{13}$C NMR (CD$_3$OD): δ 18.88, 28.07, 28.44, 29.02, 31.12, 31.31, 48.15, 54.42, 118.03, 119.13, 145.60, 146.48, 166.13; FABMS: m/e 453(M + 1), 306, 277. |
| 13f. 2HCl rac-/meso- | mp 187.5–188.5 °C (dec.). $^1$H NMR (CD$_3$OD): δ 1.39 (s, 10H), 1.65–1.80 (m, 4H), 1.85–2.08 (m, 6H), 2.17–2.27 (m, 2H), 2.62–2.80 (m, 4H), 2.97–3.15 (m, 4H), 4.29 (d, J = 4.1 Hz, 2H), 6.41 (d, J = 9.4 Hz, 2H), 7.61 (d, J = 9.4 Hz, 2H); HPLC (area %): 19.2 min. 99.0%. Analysis: Calcd. for C$_{27}$H$_{40}$N$_4$O$_2$ · 2HCl · 2H$_2$O: C, 57.75; H, 8.26; N, 9.98. Found: C, 57.87, H, 8.32; N, 9.88. |
| 13g rac-/meso- | mp 216–217° C |
| 13g. 2HCl rac-/meso- | mp 198–199 °C (dec.) $^1$H NMR (CD$_3$OD): δ 1.36(s, 12H), 1.69–1.82 (m, 4H), 1.95–2.12 (m, 6H), 2.21–2.32 (m, 2H), 2.72–2.95 (m, 4H), 2.99–3.18 (m, 4H), 4.43 (s, 2H), 6.73 (d, J = 9.3Hz, 2H), 8.01 (d, J = 9.3 Hz, 2H); $^{13}$C NMR (CD$_3$OD): δ 17.59, 25.65, 27.60, 27.83, 28.13, 30.62, 30.76, 47.46, 55.52, 115.40, 116.24, 147.44, 150.99, 164.86; FABMS: m/e 467 (M + 1), 320, 277, 246. HPLC (area %): 20.2 min. 98.4%. Analysis: Calcd. for C$_{28}$H$_{42}$N$_4$O$_2$ · 2HCl · 2.5H$_2$O: C, 57.53; H, 8.45; N, 9.58. Found: C, 57.93; H, 8.41; N, 9.53. |
| 13i rac-/meso- | mp 216–217.5° |
| 13i. 2HCl rac-/meso- | m.p. 170–172 °C.$^1$H NMR (D$_2$O): δ 1.20–1.43 (m, 16H), 1.69 (quin, J = 7.4 Hz, 4H), 1.82–2.10 (m, 6H), 2.15–2.26 (m, 2H), 2.68–2.85 (m, 4H), 3.00–3.18 (m, 4H), 4.38 (s, 2H), 6.50 (d, J = 9.3 Hz, 2H), 7.68 (d, J = 9.3 Hz, 2H); $^{13}$C NMR (CD$_3$OD): δ 17.46, 25.52, 27.39, 27.61, 27.99, 30.47, 30.70, 30.81, 47.25, 55.34, 113.38, 117.18, 146.30, 150.15, 165.15; CIMS (NH$_3$): m/e 495(M + 1), 348, 295, 201, 165, 148. HPLC (area %): 18.7 min. 99.6% Analysis: Calcd. for C$_{30}$H$_{46}$N$_4$O$_2$ · 2HCl · 2H$_2$O: C, 59.69; H, 8.68; N, 9.28; Cl, 11.75. Found: C, 59.58; H, 8.70; N, 9.44; Cl, 11.78. |
| 14e rac-/meso- | mp 201.5–202.5 °C. $^1$H NMR (CD$_3$OD): δ 0.93 (s, 6H), 1.10 (s, 6H), 1.33 (s, 8H), 1.35–1.58 (m, 6H), 1.80–1.90 (m, 2H), 2.27 (d, J = 17.1 Hz, 2H), 2.45–2.55 (m, 6H), 3.74 (dd, J = 6.8, 9.7 Hz, 2H), 6.39 (d, J = 9.4 Hz, 2H), 7.76 (d, J = 9.4 Hz, 2H); $^{13}$C NMR (CD$_3$OD): δ 25.73, 28.96, 31.08, 31.59, 31.97, 32.19, 41.87, 42.85, 46.38, 53.17, 117.87, 118.33, 143.82, 145.59, 166.12. CIMS (CH$_4$): m/e 495(M + 1), 351, 320, 193, 176, 145. |
| 14e.2 fumaric acid rac-/meso- | mp 181–182.5 °C. $^1$H NMR (D$_2$O): δ 0.91 (s, 6H), 1.16 (s, 6H), 1.32 (s, 8H), 1.58–1.78 (m, 6H), 2.07–2.18 (m, 2H), 2.43 (d, J = 17.4 Hz, 2H), 2.68 (d, J = 17.4 Hz, 2H), 2.95–3.12 (m, 4H), 4.55 (apparent t, J = 7.3 Hz, 2H), 6.56 (d, J = 9.3 Hz, 2H), 6.68 (s, 4H), 7.78 (d, J = 9.3 Hz, 2H). $^{13}$C NMR (CD$_3$OD): δ 24.85, 27.75, 27.87, 30.22, 31.52, 32.09, 38.87, 41.25, 45.40, 54.67, 110.28, 119.35, 136.50, 142.52, 148.49, 165.96, 171.63. HPLC (area %): 17.2 min. 100%. Analysis: Calcd. for C$_{30}$H$_{46}$N$_4$O$_2$ · 2C$_4$H$_4$O$_4$ · 1.5H$_2$O: C, 60.54; H 7 62; N, 7.43. Found: C, 60.27; H, 7.38; N, 7.50. The $^1$H NMR integration also matched the proposed formulation. |
| 14f rac-/meso- | mp 118–119 °C.$^1$H NMR (CD$_3$OD): δ 0.93 (s, 6H), 1.11 (s, 6H), 1.32 (s, 10H), 1.35–1.58 (m, 6H), 1.80–1.90 (m, 2H), 2.27 (d, J = 17.4 Hz, 2H), 2.43–2.56 (m, 6H), 3.74 (dd, J = 6.3, 9.6 Hz, 2H), 6.39 (d, J = 9.4 Hz, 2H), 7.76 (d, J = 9.4 Hz, 2H); $^{13}$C NMR (CD$_3$OD): δ 23.85, 27.12, 29.23, 29.71, 30.08, 30.31, 39.97, 40.95, 44.49, 51.29, 115.97, 116.44, 141.94, 143.71, 164.24. FABMS: m/e 509(M + 1, 15), 334 (100). |
| 14f. 2 fumaric acid rac-/meso- | mp 158–159.5° C. $^1$H NMR (D$_2$O): δ 0.91(s, 6H), 1.16 (s, 6H), 1.30 (s, br, 10H), 1.58–1.78 (m, 6H), 2.08–2.18 (m, 2H), 2.43 (d, J = 17.4 Hz, 2H), 2.68 (d, J = 17.4 Hz, 2H), 2.95–3.12 (m, 4H), 4.55 (apparent t, J = 7.2 Hz, 2H), 6.56 (d, J = 9.4 Hz, 2H), 6.65 (s, 4H), 7.79 (d, J = 9.4 Hz, 2H). $^{13}$C NMR:(CD$_3$OD): δ 24.68, 27.20, 27.25, 29.56, 29.71, 31.24, 31.62, 38.43, 40.89, 45.21, |

TABLE IA-continued

| Compound No./Isomer | Characterising Data |
|---|---|
| | 54.38, 110.96, 118.59, 136.31, 142.83, 148.53, 166.02, 173.16.HPLC (area %): 18.0 min. 98.4%. Analysis: Calcd. for $C_{31}H_{48}N_4O_2 \cdot 2C_4H_4O_4 \cdot 3.5H_2O$: C, 58.27; H, 7.90; N, 6.97. Found: C, 58.22; H, 7.63; N, 7.22. The $^1H$ NMR integration also matched the proposed formulation. |
| 14g rac-/meso- | mp 158–160 °C. $^1H$ NMR (CD$_3$OD): δ 0.93 (s, 6H), 1.11 (s, 6H), 1.31 (s, 12H), 1.38–1.58 (m, 6H), 1.80–1.90 (m, 2H), 2.27 (d, J = 17.2 Hz, 2H), 2.45–2.55 (m, 6H), 3.74 (dd, J = 6.1, 9.6 Hz, 2H), 6.39 (d, J = 9.4 Hz, 2H), 7.76 (d, J = 9.4 Hz, 2H); $^{13}C$ NMR (CD$_3$OD): δ 25.73, 29.01, 31.15, 31.59, 31.98, 32.20, 41.86, 42.82, 46.36, 53.16, 117.85, 118.33, 143.82, 145.61, 166.12. FABMS(CH$_4$): m/e 523(M + 1, 18), 348 (100). |
| 14g.2 fumaric acid rac-/meso- | mp 155.5–157 °C.$^1H$ NMR (D$_2$O): δ 0.92 (s, 6H), 1.16 (s, 6H), 1.28 (s, br, 12H), 1.58–1.80 (m, 6H), 2.07–2.18 (m, 2H), 2.43 (d, J = 17.4 Hz, 2H), 2.68 (d, J = 17.4 Hz, 2H), 2.95–3.12 (m, 4H), 4.55 (apparent t, J = 7.6, Hz, 2H), 6.56 (d, J = 9.4 Hz, 2H), 6.66 (s, 4H), 7.79 (d, J = 9.4 Hz, 2H). $^{13}C$ NMR (CD$_3$OD): δ 24.69, 27.21, 27.28, 29.64, 29.90, 31.26, 31.65, 38.44, 40.91, 45.19, 54.38, 110.97, 118.63, 136.28, 142.81, 148.54, 166.01, 172.92. HPLC (area %): 18.8 min. 100%. Analysis: Calcd. for $C_{32}H_{50}N_4O_2 \cdot 2C_4H_4O_4 \cdot 3H_2O$: C, 59.39; H, 7.97; N, 6.93. Found: C, 59.00; H, 7.63; N, 7.25. |
| 14i rac-/meso- | mp 134–136° C. $^1H$ NMR (CD$_3$OD): δ 0.93 (s, 6H), 1.11 (s, 6H), 1.31 (s, 16H), 1.38–1.58 (m, 6H), 1.80–1.90 (m, 2H), 2.27 (d, J = 17.2 Hz, 2H), 2.45–2.56 (m, 6H), 3.74 (dd, J = 6.1, 9.6 Hz, 2H), 6.39 (d, J = 9.4 Hz, 2H), 7.77 (d, J = 9.4 Hz, 2H); $^{13}C$ NMR (CD$_3$OD): δ 25.74, 29.01, 31.18, 31.60, 31.97, 32.21, 41.85, 42.84, 46.37, 53.15, 117.87, 118.32, 143.82, 145.59, 166.13. FABMS: m/e 551(M + 1, 18), 376 (100), 201 (85). |
| 14i.2 fumaric acid rac-/meso- | mp 160–161 °C.$^1H$ NMR (D$_2$O): δ 0.91 (s, 6H), 1.16 (s, 6H), 1.20–1.40 (m, 16H), 1.58–1.80 (m, 6H), 2.07–2.18 (m, 2H), 2.43 (d, J = 17.3 Hz, 2H), 2.68 (d, J = 17.3 Hz, 2H), 2.95–3.12 (m, 4H), 4.56 (apparent t, J = 7.4 Hz, 2H), 6.56 (d J = 9.4 Hz, 2H), 6.66 (s, 4H), 7.78 (d, J = 9.4 Hz, 2H). $^{13}C$ NMR (CD$_3$OD): δ 24.67, 27.13, 27.20, 29.57, 29.91, 30.09, 31.25, 31.58, 38.40, 40.87, 45.21, 54.33, 111.10, 118.50, 136.24, 142.91, 148.55, 166.06, 173.11. HPLC (area %): 20.4 min. 99.8%. Analysis: Calcd. for $C_{34}H_{54}N_4O_2 \cdot 2C_4H_4O_4 \cdot 2.5H_2O$: C, 60.92; H, 8.16; N, 6.77. Found: C, 61.10; H, 7.82; N, 7.08. The $^1H$ NMR integration also matched the proposed formulation. |
| 15i rac-/meso- | mp 107–109 °C.$^1H$ NMR (CDCl$_3$): δ 1.27 (s, br, 16H), 1.40–1.53 (m, 4H), 1.60–1.71 (m, 2H), 1.72–1.88 (m, 4H), 1.90–2.05 (m, 2H), 2.47–2.73 (m, 8H), 3.48 (s, 6H), 3.54 (t, J = 4.2 Hz, 2H), 6.47 (d, J = 9.3 Hz, 2H), 7.33(d, J = 9.3 Hz, 2H); $^{13}C$ NMR (CDCl$_3$): δ 17.61, 26.42, 27.38, 27.49, 29.54, 29.57, 30.20, 30.52, 47.37, 53.90, 117.30, 117.51, 140.69, 144.65, 163.25; EIMS: m/e : 523(M + 1), 360, 177, 162. |
| 15i. 2–fumaric–acid rac-/meso- | mp 168–169° C. $^1H$ NMR(CD$_3$OD): δ 1.22–1.45 (m, 16H); 1.62–1.78 (m, 4H), 1.88–2.08 (m, 6H), 2.15–2.26 (m, 2H), 2.70–3.12 (m, 8H), 3.54 (s, 6H), 4.31 (s, 2H), 6.49 (d, J = 9.4 Hz, 2H), 6.65 (s, 4H), 7.58 (d, J = 9.4 Hz, 2H); $^{13}C$ NMR (CD$_3$OD): δ 17.97, 25.00, 27.82, 28.13, 28.32, 30.66, 30.83, 31.04, 31.67, 47.27, 56.66, 112.04, 117.95, 136.76, 143.02, 151.14, 165.69, 171.89; HPLC (area %): 19.2 min. 97.1%. Analysis: Calcd. for $C_{32}H_{50}N_4O_2 \cdot 2C_4H_4O_4 \cdot 1.5H_2O$: C, 61.44; H, 7 86; N, 7.16. Found: C, 61.49; H, 7.75; N, 7.27. The $^1H$ NMR integration also matched the proposed formulation. |
| 17i rac-/meso- | colorless oil. $^1H$ NMR (CDCl$_3$): δ 1.26 (s, br, 18H), 1.42–1.55 (m, 4H), 1.72–1.90 (m, 6H), 1.90–2.04 (m, 2H), 2.55–2.88 (m, 8H), 3.69 (t, J 4.7Hz, 2H), 3.88 (s, 6H), 6.53 (d, J = 8.4 Hz, 2H), 7.55 (d, J = 8.4 Hz, 2H). $^{13}C$ NMR (CDCl$_3$): δ 18.73, 27.36, 28.08, 29.53, 30.50, 32.28, 47.03, 53.17, 54.46, 107.75, 127.10, 139.55, 154.64, 162.22. CIMS (CH$_4$): m/e 523 (M + 1, 90), 360 (55), 162 (100). |
| 17i.2 fumaric acid rac-/meso- | mp 188–190° C. $^1H$ NMR (CD$_3$OD): δ 1.22–1.42 (m, 16H), 1.71 (quin, J = 7.4Hz, 4H), 1.90–2.11 (m, 6H), |

TABLE IA-continued

| Compound No./Isomer | Characterising Data |
| --- | --- |
| | 2.15–2.27 (m, 2H), 2.72–3.10 (m, 8H), 3.89 (s, 6H), 4.44 (t, J = 4.2 Hz, 2H), 6.63 (s, 4H) 6.71 (d, J = 8.6 Hz, 2H), 7.77 (d, J = 8.6 Hz, 2H). $^{13}$C NMR (CD$_3$OD): δ 19.04, 26.31, 27.62, 28.08, 30.58, 30.80, 30.96, 32.70, 46.92, 55.04, 56.75, 109.65, 120.50, 136.71, 142.62, 158.48, 165.90, 172.15. HPLC (area %): 22.2 min. 96.3%. Analysis: Calcd. for C$_{32}$H$_{50}$N$_4$O$_2$ · 2C$_4$H$_4$O$_4$ : C, 63.64; H, 7.74; N,7.42. Found: C, 63.55; H, 7.82; N, 7.64. The $^1$H NMR also matched the proposed formulation. |
| 22g (S, S)-(–)- | mp 170–171.5° C; [α]$^{20}_D$ = 97.2° (c = 1, CHCl$_3$). $^1$H NMR (CDCl$_3$): δ 1.29 (s, 8H), 1.62 (apparent t, J = 6.6 Hz, 4H), 1.70–1.80 (m, 2H), 1.86 (quin, J = 5.9 Hz, 4H), 1.92–2.03 (m, 2H), 2.15 (t, J = 7.5 Hz, 4H), 2.70–2.88 (m, 4H), 5.07–5.14 (m, 2H), 5.32 (s, 4H), 5.77 (d, J = 8.6 Hz, 2H), 6.59 (d, J = 8.5 Hz, 2H), 7.26–7.46 (m, 12H).$^{13}$C NMR (CDCl$_3$): δ 19.59, 25.68, 29.00, 29.07, 29.84, 32.07, 36.81, 46.27, 67.43, 109.05, 124.92, 127.71, 128.05, 128.34, 137.39, 139.49, 154.73, 162.05, 172.40. CIMS (NH$_3$): m/e 675 (M + 1, 48), 583 (30), 296 (25), 271 (26), 255 (64), 238 (100), 148 (16). Analysis: Calcd. for C$_{42}$H$_{50}$N$_4$O$_4$ · 0.1H$_2$O: C, 74.55; H, 7.48; N, 8.28. Found: C, 74.31; H, 7.59; N, 8.56. |
| 23g (S, S)-(–)- | mp 59–61° C, [α]$^{20}_D$ = 25.8° (c = 1, CHClhd 3). $^1$H NMR (CDCl$_3$): δ 1.28 (s, 14H), 1.4–1.55(m, 4H), 1.70–1.89 (m, 6H), 1.90–2.05 (m, 2H), 2.56–2.89 (m, 8H), 3.69 (t, J = 4.5 Hz, 2H), 6.59 (d, J = 8.4 Hz, 2H), 7.26–7.46 (m, 10H), 7.56(d, J = 8.4 Hz, 2H). $^{13}$C NMR (CDCl$_3$): δ 18.77, 27.40, 28.12, 29.53, 30.54, 32.31, 47.09, 54.53, 67.36, 108.30, 127.35, 127.63, 128.05, 128.33, 137.65, 139.69, 154.62, 161:72. CIMS (NH$_3$): m/e 647 (M + 1, 16), 408 (16), 255 (24), 238 (100). Analysis: Calcd. for C$_{42}$H$_{54}$N$_4$O$_2$: C, 77.98; H, 8.41; N, 8.66. Found: C, 77.95; H, 8.65; N, 8.82. |
| 13g (S, S)-(–)- | m.p. 198–199° C, [a]$^{20}_D$ = 45.5° (c =0.4, MeOH—CHCl$_3$ 1:1). |
| 13g. 2 HCl (S, S)-(–)- | m.p. 190–191° C. [α]$^{20}_D$ = –56.0° (c = 1, MeOH). $^1$H NMR (D$_2$O): δ 1.21–1.44 (m, 12H), 1.69 (quin, J = 6.8Hz, 4H), 1.82–2.10 (m, 6H), 2.15–2.26 (m, 2H), 2.68–2.85 (m, 4H), 3.00–3.18 (m, 4H), 4.38 (s, 2H), 6.52 (d, J = 9.3 Hz, 2H), 7.69 (d, J = 9.3Hz, 2H); $^{13}$C NMR (D$_2$O + CD$_3$OD): δ 16.78, 24.95, 26.87, 27.09, 29.42, 29.63, 46.76, 54.75, 114.35, 116.19, 146.72, 149.99, 165.06; MS (NH$_3$): m/e 467 (M + 1), 255, 238, 173, 148. HPLC (area %): 16.7min. 97.6% Analysis: Calcd. for C$_{28}$H$_{42}$N$_4$O$_2$ · 2HCl · 5H$_2$O: C, 59.35; H, 8.36; N, 9.89; C1, 12.51. Found: C, 59.42; H, 8.14; N, 9.98; Cl, 12.79. |
| 22h (S, S)-(–)- | mp 185–187° C, [α]$^{20}_D$ = –93.8° ( c = 1, CHCl$_3$). $^1$H NMR (CDCl$_3$): δ 1.28 (s, 10H), 1.63 (apparent t, J = 6.6 Hz, 4H), 1.70–1.81 (m, 2H), 1.87 (quin, J = 5.8 Hz, 4H), 1.92–2.03 (m, 2H), 2.16 (t, J = 7.5 Hz, 4H), 2.70–2.88 (m, 4H), 5.07–5.15 (m, 2H), 5.33 (s, 4H), 5.72 (d, J = 8.5 Hz, 2H), 6.59 (d, J = 8.5 Hz, 2H), 7.26–7.46 (m, 12H). $^{13}$C NMR (CDCl$_3$): δ 19.52, 25.59, 28.92, 28.96, 29.76, 31.80, 36.78, 46.19, 67.81, 109.04, 125.19, 127.81, 128.02, 128.39, 137.14, 140.02, 154.56, 161.87, 172.53. CIMS (NH$_3$): m/e 689 (M + 1, 70), 597 (36), 271 (40), 255 (58), 238 (100), 188 (20), 148 (45). Analysis: Calcd. for C$_{43}$H$_{52}$N$_4$O$_4$ · 0.2H$_2$O: C, 74.58; H, 7.63; N, 8.09. Found: C, 74.28; H, 7.68; N, 8.51. |
| 23h | mp 52–53° C, [α]$^{20}_D$ = –24.9° (c = 1, CHCl$_3$). $^1$H NMR (CDCl$_3$): δ 1.27 (s, 16H), 1.4–1.55(m, 4H), 1.70–1.89 (m, 6H), 1.90–2.05 (m, 2H), 2.55–2.89 (m, 8H), 3.69 (t, J = 4.5 Hz, 2H), 6.59 (d, J = 8.4 Hz, 2H), 7.26–7.46 (m, 10H), 7.56(d, J = 8.4 Hz, 2H). $^{13}$C NMR (CDCl$_3$): δ 18.75, 27.40, 28.10, 29.54, 29.56, 30.52, 32.30, 47.08, 54.51, 67.35, 108.29, 127.34, 127.63, 128.04, 128.32, 137.63, 139.68, 154.61, 161.71. CIMS (NH$_3$): m/e 661 (M + 1, 40), 422 (40), 255 (15), 238 (100), 148 (10). Analysis: Calcd. for C$_{43}$H$_{56}$N$_4$O$_2$: C, 78.14; H, 8.54; N, 8.48. Found: C, 78.08; H, 8.53; N, 8.44. |
| 13h (S, S)-(–)- | mp 187–189° C, [α]$^{20}_D$ = –41.0° (c =0.4, MeOH—CHCl$_3$ 1:1) |

TABLE IA-continued

| Compound No./Isomer | Characterising Data |
|---|---|
| 13h. 2 HCl<br>(S, S)-(−)- | solid foam. $[\alpha]^{20}_D = -51.5°$ (c = 1, MeOH). $^1$H NMR (D$_2$O): δ 1.20–1.43 (m, 14H), 1.70 (quin, J = 7.1 Hz, 4H), 1.82–2.10 (m, 6H), 2.15–2.26 (m, 2H), 2.68–2.85 (m, 4H), 3.00–3.18 (m, 4H), 4.39 (s, 2H), 6.51 (d, J = 9.3 Hz, 2H), 7.69 (d, J = 9.3Hz, 2H); $^{13}$C NMR (CD$_3$OD): δ 17.44, 25.45, 27.39, 27.57, 27.95, 30.42, 30.63, 47.20, 55.28, 113.92, 116.75, 146.62, 150.33, 164.95; MS (NH$_3$): m/e 481(M + 1), 187, 148. HPLC (area %): 17.8 min. 98.6%.<br>Analysis: Calcd. for C$_{29}$H$_{44}$N$_4$O$_2$ · 2.6HCl · 2.5H$_2$O: 56.13; H, 8.38; N, 9.03; Cl, 14.85. Found: C, 56.10; H, 8.14; N, 9.18; Cl; 15.16. |
| 22j<br>(S, S)-(−)- | mp 179–180° C, $[\alpha]^{20}_D = -90.1°$ (c = 1, CHCl$_3$). $^1$H NMR (CDCl$_3$): δ 1.27 (s, 14H), 1.62 (apparent t, J = 6.6 Hz, 4H), 1.70–1.80 (m, 2H), 1.86 (quin, J = 5.8 Hz, 4H), 1.92–2.04 (m, 2H), 2.16 (t, J = 7.5 Hz, 4H), 2.70–2.88 (m, 4H), 5.07–5.15 (m, 2H), 5.32 (s, 4H), 5.74 (d, J = 8.5 Hz, 2H), 6.59 (d; J = 8.4 Hz, 2H), 7.26–7.46 (m, 12H). $^{13}$C NMR (CDCl$_3$): δ 19.59, 25.76, 29.15, 29.27, 29.84, 32.07, 36.90, 46.27, 67.44, 109.06, 124.92, 127.72, 128.05, 128.34, 137.39, 139.51, 154.74, 162.05, 172.47. CIMS (NH$_3$): m/e 717 (M + 1, 10), 255(100), 238 (70).<br>Analysis: Calcd. for C$_{45}$H$_{56}$N$_4$O$_4$: C, 75.39; H, 7.87; N, 7.81. Found: C, 75.45; H, 7.83; N, 7.92. |
| 23j<br>(S, S)-(−)- | mp 61–63° C, $[\alpha]^{20}_D = -24.7°$ (c = 1, CHCl$_3$).<br>$^1$H NMR (CDCl$_3$): δ 1.26 (s, 20H), 1.4–1.55(m, 4H), 1.70–1.89 (m, 6H), 1.90–2.05 (m, 2H), 2.55–2.89 (m, 8H), 3.69 (t, J = 4.5 Hz, 2H), 6.59 (d, J = 8.4 Hz, 2H), 7.26–7.46 (m, 10H), 7.56(d, J = 8.4 Hz, 2H). $^{13}$C NMR (CDCl$_3$): δ 18.76, 27.41, 28.10, 29.59, 29.56, 30.53, 32.31, 47.09, 54.52, 67.35, 108.30, 127.34, 127.63, 128.05, 128.32, 137.64, 139.69, 154.62, 161.72. CIMS (NH$_3$): m/e 689 (M + 1, 35), 450 (40), 238 (100), 148 (10).<br>Analysis: Calcd. for C$_{45}$H$_{60}$N$_4$O$_2$: C, 78.45; H, 8.78; N, 8.13. Found: C, 78.48; H, 8.74; N, 8.19. |
| 13j<br>(S, S)-(−)- | mp 204–206° C, $[\alpha]^{20}_D = -42.5°$ (c = 0.4, MeOH—CHCl$_3$ 1:1). |
| 13j. 2HCl<br>(S,S)-(−)- | solid foam. $[\alpha]^{20}_D = -48.8°$ (c = 1, MeOH). $^1$H NMR (D$_2$O): δ 1.20–1.43(m, 18H), 1.69(quin, J = 7.4 Hz, 4H), 1.82–2.10(m, 6H), 2.15–2.26(m, 2H), 2.68–2.85(m, 4H), 3.00–3.18(m, 4H), 4.38(s, 2H), 6.52(d, J = 9.3Hz, 2H), 7.69(d, J = 9.3 Hz, 2H); $^{13}$C NMR (CD$_3$OD): δ 17.33, 25.16, 27.56, 27.62, 27.96, 30.46, 30.69, 30.80, 30.86, 47.35, 54.93, 113.29, 119.67, 149.78, 152.21, 163.37; MS (NH$_3$): m/e 509(M + 1), 510 (M + 2), 295, 216, 148. HPLC (area %): 19.6 min. 98.8%<br>Analysis: Calcd. for C$_{31}$H$_{48}$N$_4$O$_2$ · 2.8HCl · 2.5H$_2$O: C, 56.77; H, 8.58; N, 8.54; Cl, 15.14. Found: C, 56.97; H, 8.42; N, 8.72; Cl, 15.10. |
| 23j<br>(S, S)-(−)- | mp 61–63° C, $[\alpha]^{20}_D = -24.7°$ (c = 1, CHCl$_3$).<br>$^1$H NMR (CDCl$_3$): δ 1.26 (s, 20H), 1.4–1.55(m, 4H), 1.70–1.89 (m, 6H), 1.90–2.05 (m, 2H), 2.55–2.89 (m, 8H), 3.69 (t, J = 4.5 Hz, 2H), 6.59 (d, J = 8.4 Hz, 2H), 7.26–7.46 (m, 10H), 7.56(d, J = 8.4 Hz, 2H) $^{13}$C NMR (CDCl$_3$): δ 18/76, 27.41, 28.10, 29.56, 30.53, 32.31, 47.09, 54.52, 67.35, 108.30, 154.62, 161.72, 128.05, 128.32, 137.64, 139.69, 154.62, 161.72. CIMS (NH$_3$): m/e 689 (M + 1, 35), 450 (40), 238<br>Analysis: Calcd. for C$_{45}$H$_{60}$N$_4$O$_2$: C, 78.45; H, 8.78; N, 8.13. Found: C, 78.48; H: 8.74; N, 8.19. |
| 13j<br>(S, S)-(−)- | mp 204–206° C., $[\alpha]^{20}_D = -48.8°$ (c = 1, MeOH). $^1$H NMR 1:1) |
| 13j. 2HCl<br>(S, S)-(−)- | solid foam, $[\alpha]^{20}_D = -48.8°$ (c = 1, MeOH). $^1$H NMR (D$_2$O): δ 1.20–1.43(m, 18H), 1.69(quin, J = 7.4 Hz, 4H), 1.82–2.10(m, 6H), 2.15–2.26(m, 2H), 2.68–2.85(m, 4H), 3.00–3.18(m, 4H), 4.38(s, 2H), 6.52(d, J = 9.3 Hz, 2H), 7.69(d, J = 9.3 Hz, 2H); $^{13}$C NMR (CD$_3$OD): δ 17.33, 25.16, 27.56, 27.62, 30.46, 30.69, 30.80, 30.86, 47.35, 54.93, 113.29, 119.67, 149.78, 153.21, 163.37; MS (NH$_3$): m/e 509(M + 1), 510 (M + 2), 295, 216, 148. HPLC (area %): 19.6 min. 98.8%<br>Analysis: Calcd. for C$_{31}$H$_{48}$N$_4$O$_2$ · 2.8HCl · 2.5H$_2$O : C, 56.77; H, 8.58; N, 8.54; Cl, 15.14. Found: C, 56.97; H, 8.42; N, 8.72; Cl, 15.10. |
| 22k | mp 155–157° C, $[\alpha]^{20}_D = -89.70°$ (c = 1, CHCl$_3$). $^1$H |

TABLE IA-continued

| Compound No./Isomer | Characterising Data |
| --- | --- |
| (S, S)-(−)- | NMR (CDCl$_3$): δ 1.2 (apparent d, J = 6.4 Hz, 16H), 1.62 (apparent t, J = 6.6 Hz, 4H), 1.70–1.80 (m, 2H), 1.86 (quin, J = 5.8 Hz, 4H), 1.90–2.03 (m, 2H), 2.16 (t, J = 7.5 Hz, 4H), 2.70–2.88 (m, 4H), 5.07–5.15 (m, 2H), 5.32 (s, 4H), 5.79 (d, J = 8.6 Hz, 2H), 6.59 (d, J = 8.4 Hz, 2H), 7.26–7.46(m, 12H). $^{13}$C NMR (CDCl$_3$): δ 19.60, 25.79, 29.19, 2Q22, 29.36, 29.41, 29.84, 32.08, 36.89, 46.26, 67.43, 109.05, 124.94, 127.71, 128.04, 128.34, 137.40, 139.49, 154.73, 162.04, 172.48. CIMS (NH$_3$): m/e 731 (M + 1, 24), 639 (10), 255 (60), 238 (100), 146 (15). Analysis: Calcd. for C$_{46}$H$_{58}$N$_4$O$_4$: C, 75.58; H, 8.00; N, 7.66. Found: C, 75.74; H, 7.93; N, 7.78. |
| 23k (S, S)-(−)- | waxy oil [α]$^{20}$$_D$ = −23.1° (c = 1, CHCl$_3$). $^1$H NMR (CDCl$_3$): δ 1.26 (s, 22H), 1.4–1.55(m, 4H), 1.70–1.89 (m, 6H), 1.90–2.05 (m, 2H), 2.55–2.89 (m, 8H), 3.69 (t, J = 4.5 Hz, 2H), 6.59 (d, J = 8.4 Hz, 2H), 7.26–7.47 (m, 10H), 7.56(d, J = 8.4 Hz, 2H). $^{13}$C NMR (CDCl$_3$): δ 18.77, 27.41, 28.13, 29.56, 29.60, 30.55, 32.31, 47.10, 54.53, 67.36, 108.30, 127.38, 127.63, 128.05, 128.32, 137.66, 139.69, 154.62, 161.72. CIMS (NH$_3$): m/e 703 (M + 1, 16), 464 (15), 255 (10), 238 (100). |
| 13k (S, S)-(−)- | mp 205–207° C., [α]$^{20}$$_D$ = 42.0° (c = 0.4, MeOH—CHCl$_3$ 1:1). |
| 13k. 2HCl (S, S)-(−)- | m.p. 167–169° C. [α]$^{20}$$_D$ = −49.6° (c = 1, MeOH). $^1$H NMR (D$_2$O): δ 1.20–1.42 (m, 20H), 1.69 (quin, J = 7.4 Hz, 4H), 1.82–2.10 (m, 6H), 2.15–2.26 (m, 2H), 2.68–2.84 (m, 4H), 3.00–3.18 (m, 4H), 4.38 (s, 2H), 6.51 (d, J = 9.3Hz, 2H), 7.68 (d, J = 9.3 Hz, 2H); $^{13}$C NMR (CD$_3$OD): δ 17.31, 25.15, 27.60, 27.98, 30.50, 30.75, 30.87, 30.94, 47.30, 54.96, 113.50, 119.33, 149.56, 152.11, 163.51; CIMS (NH$_3$): m/e 523 (M + 1), 376, 295, 229.HPLC (area %): 20.6 min. 99.3% Analysis: Calcd. for C$_{32}$H$_{50}$N$_4$O$_2$ · 2.1HCl · 1.5H$_2$O : C, 61.36; H, 8.87; N, 8.94; Cl, 11.89. Found: C, 61.06; H, 9.10; N, 9.06; Cl, 11.84. |
| 22i (S, S)-(+)- | mp 175–177° C, [α]$^{20}$$_D$ = + 91.40 (c = 1, CHCl$_3$). $^1$H NMR (CDCl$_3$): δ 1.28 (s, 12H), 1.63 (quin, J = 6.9 Hz, 4H), 1.70–1.82 (m, 2H), 1.87 (quin, J = 5.9 Hz, 4H), 1.93–2.05 (m, 2H), 2.16 (t, J = 7.6 Hz, 4H), 2.70–2.89 (m, 4H), 5.08–5.17 (m, 2H), 5.33 (s, 4H), 5.71 (d, J = 8.6 Hz, 2H), 6.59 (d, J = 8.5 Hz, 2H), 7.26–7.46 (m, 12H). $^{13}$C NMR (CDCl$_3$): δ 19.64, 25.76, 29.17, 29.27, 29.92, 32.12, 36.94, 46.33, 67.46, 109.12, 124.99, 127.72, 128.07, 128.36, 137.51, 139.52, 154.79, 162.14, 172.40.CIMS (CH$_4$): m/e 703 (M + 1, 100), 611 (50), 238 (95), 148 (30). Analysis: Calcd. for C$_{44}$H$_{54}$N$_4$O$_4$: C, 75.18; H, 7.74; N, 7.97. Found: C, 75.03; H, 7.75; N, 8.19. |
| 23i (R, R)-(+)- | mp 52–54° C, [α]$^{20}$$_D$ = +25.5° (c = 1, CHCl$_3$). $^1$H NMR (CDCl$_3$): δ 1.26 (s, 18H), 1.48 (quin, J = 6.6 Hz, 4H), 1.70–1.89 (m, 6H), 1.90–2.05 (m, 2H), 2.56–2.89 (m, 8H), 3.69 (t, J = 4.6 Hz, 2H), 6.59 (d, J = 8.4 Hz, 2H), 7.26–7.47 (m, 10H), 7.56(d, J = 8.4 Hz, 2H). $^{13}$C NMR (CDCl$_3$): δ 18.85, 27.43, 28.27, 29.58, 30.60, 32.35, 47.13, 54.61, 67.37, 108.33, 127.46, 127.62, 128.06, 128.33, 137.77, 139.67, 154.66, 161.78. CIMS (CH$_4$): m/e 675 (M + 1, 18), 436 (20), 255 (20), 238 (100). Analysis: Calcd. for C$_{44}$H$_{58}$N$_4$O$_2$ · 0.1H$_2$O: C, 78.09; H, 8.67; N, 8.28. Found: C, 77.88; H, 8.86; N, 8.50. |
| 13i (R, R)-(+)- | mp 193–195° C, [α]$^{20}$$_D$ = +42.00 (c = 0.4, MeOH—CHCl$_3$ 1:1). |
| 13i. 2HCl (R, R)-(+)- | m.p. 182–184° C. [α]$^{20}$$_D$ = +51° (c = 1, MeOH). H NMR (D$_2$O): δ 1.20–1.43 (m, 16H), 1.69 (quin, J = 7.4 Hz, 4H), 1.82–2.10 (m, 6H), 2.15–2.26 (m, 2H), 2.68–2.85(m, 4H), 3.00–3.18 (m, 4H), 4.38 (s, 2H), 6.51 (d, J = 9.3 Hz, 2H), 7.68 (d, J 9.3 Hz, 2H); $^{13}$C NMR (CD$_3$OD): δ 17.37, 25.33, 27.54, 27.95, 30.42, 30.64, |

TABLE IA-continued

| Compound No./Isomer | Characterising Data |
|---|---|
| | 30.74, 47.36, 55.09, 115.13, 116.98, 148.36, 151.29, 164.89; MS (NH$_3$): m/e 495 (M + 1, 8), 295 (15), 201 (76), 165 (12), 148 (100). HPLC (area %): 18.7 min. 95.8% Analysis: Calcd. for C$_{30}$H$_{46}$N$_4$O$_2$ · 2.5HCl · 2H$_2$O : C, 57.94; H, 8.51; N, 9.01; Cl, 14.25. Found: C, 57.88; H, 8.25; N, 9.15; Cl, 13.88. |

EXAMPLE 9

Cholinesterase Inhibition by rac-/meso-Dimeric Compounds

Cholinesterase assays were carried out using the Ellman method (Ellman, G. L.; Courtney, K. D.; Andreas, V. J.; Featherstone, R. M.; *Biochem. Pharm.*, 1961, 7, 88–95). AChE and BChE enzyme preparations were prepared from cortex and serum respectively of decapitated rats. Frontal cortex (brain dissected on ice) was homogenized in sodium phosphate buffer (39 vol. 75 mM, pH 7.4). Rat serum was obtained by centrifugation of blood (3500×g, 10 min.). The cholinesterase assays were performed using the cloroimetric method of Ellman, with minor modification. For determination of AChE inhibition, cortex homogenate was preincubated for 5 minutes with ethopropazine (0.1 mM), a selective inhibitor of BChE. Similarly, for determination of BChE inhibition, serum was preincubated with BW284c51 (0.01 mM), a selective inhibitor of AChE. A mixture of 4 mL containing acetylthiocholine iodide (0.3 mM) or butrylthiocholine iodide (0.4 mM), I mL sodium phosphate buffer (0.1 mM, pH 7.4), a solution of the compound being tested (0.1 mL), and homogenate or serum (0.1 mL) was incubated at 37° C. for 8 minutes. The reaction was terminated by the addition of sodium dodecyl sulfate (3% w/v, 1 mL), after which the 5,5'-dithiobis-(2-nitrobenzoic acid) indicator (0.2% w/v, 1 mL) was added. Enzyme activity was determined by measuring the absorbance at 420 nm after 10 minutes, relative to the drug-free control. Triplicate measurements were performed at typically a total of 8 drug concentrations; IC$_{50}$ values were determined from a plot of Enzyme Activity vs. -log[drug].

The results of the assays are given in Table II below:

TABLE II

Cholinesterase inhibition by rac-lmeso-dimers

| Entry | Drug[2] | n | AchE IC50 (nM)[b] | BchE IC50 (nM)[c] | Selectivity for AChE[d] |
|---|---|---|---|---|---|
| 1 | (±)-16 | na | ·500,000[e] | ·500,000[e] | ·1 |
| 2 | rac-lmeso-13a | 4 | 42,300 ± 3,500 | 115,400 ± 3,800 | 2.7 |
| 3 | rac-lmeso-13b | 5 | 10,512 ± 2,014 | 96,016 ± 1,192 | 9.1 |
| 4 | rac-lmeso-13c | 6 | 3,763 ± 818 | 98,823 ± 21,114 | 26.3 |
| 5 | rac-lmeso-13d | 7 | 1,236 ± 68 | 34,607 ± 2,079 | 28.0 |
| 6 | rac-lmeso-13e | 8 | 1,166 ± 184 | 10,185 ± 130 | 8.7 |
| 7 | rac-lmeso-13f | 9 | 356 ± 7 | 10,765 ± 130 | 30.3 |
| 8 | rac-lmeso-13g | 10 | 239 ± 18 | 5,455 ± 102 | 22.8 |
| 9 | rac-lmeso-13i | 12 | 159 ± 26 | 24,432 ± 913 | 153 |
| 10 | rac-lmeso-14d | 7 | 18,300 ± 2,600 | 190,000 ± 70,600 | 10 |
| 11 | rac-lmeso-14e | 8 | 22,300 ± 2,300 | 89,900 ± 12,100 | 4.0 |
| 12 | rac-lmeso-14f | 9 | 11,800 ± 280 | 104,000 ± 8,300 | 8.8 |
| 13 | rac-lmeso-14g | 10 | 6,110 ± 230 | 105,000 ± 5,800 | 17 |
| 14 | rac-lmeso-14i | 12 | 3,620 ± 110 | 60,000 ± 3,200 | 17 |
| 15 | rac-lmeso-15g | 10 | 438 ± 29 | 76,600 ± 6,800 | 180 |
| 16 | rac-lmeso-15i | 12 | 355 ± 16 | 74,300 ± 6,800 | 210 |
| 17 | rac-lmeso-17g | 10 | 4,531 ± 442 | 34,560 ± 289 | 7.6 |
| 18 | rac-lmeso-17i | 12 | 5,000 ± 190 | 78,900 ± 14,500 | 15.8 |
| 19 | rac-lmeso-19g | 10 | 1,860 ± 120 | 12,300 ± 240 | 6.6 |
| 20 | (–)-huperzine A[f] | na | 115 ± 1 | 135,000 ± 6,000 | 1,200 |
| 21 | lacrine | na | 231 ± 16 | 77.2 ± 5.8 | 0.3 |

[a]Drugs 13, 16 were assayed as the hydrochloride salts; drugs 14, 15, 17, 19 were assayed as the fumaric acid salts. Elemental analyses matched the proposed salt formulations (C, H, N, Cl ± 0.4%).
[b]Assay performed using rat cortex homogenate, in the presence of ethopropazine as a specific BChE inhibitor.
[c]Assay performed using rat serum, in the presence of BW284c51 as a specific AChE inhibitor.
[d]Selectivity for AChE is defined as IC$_{50}$(BChE)/IC$_{50}$(AChE).
[e]Estimated values based on ~50% inhibition of AChE and BChE at 0.5 mM, the highest drug concentration tested.
[f]Measured $[\alpha]_D^{20} = -149°$ (c = 0.17, CHCl$_3$); literature (ref. 3a): $[\alpha]_D^{25} = -150°$ (c = 0.12, CHCl$_3$).

As expected, monomeric control (±)-16 was an extremely weak AChE inhibitor (IC$_{50}$ ~500,000 nM. Table II, entry 1). However corresponding dimers rac-/meso-13a-g,i showed dramatically enhanced potency, with the highest potency observed at a tether length of 12 methylenes (rac-/meso-13i, 159 nM, entry 9). The dimers rac-/meso-14d-g,i derived from 11 displayed a similar optimization of potency at n=12, but proved less potent than rac-/meso-13i (cf. entries 9, 14). Finally, dimers 19 derived from 5-amino-2-benzyloxy-5,6, 7,8-tetrahydro-5-methylquinoline proved somewhat unstable upon removal of the O-benzyl group, and only 19 g was purified and assayed; it proved to be 8-fold less potent than 13 g. Thus, it would appear that optimal affinity can be obtained by avoiding both C-9 and C-5 alkylation.

To test whether both hydrogen bonding of the pyridone moiety of rac-/meso-13i with the AChE catalytic site contributes to affinity, 2-methoxypyridine analogs rac-/meso-17 g,i were assayed. The 31-fold increase in AChE IC$_{50}$ of rac-/meso-17i relative to rac-/meso-13i (cf. entries 9, 16) is consistent with the loss of the pyridone NH hydrogen bond donor, and steric hindrance of hydrogen bonding to the ether oxygen. Similarly, the N-methyl quinolinone dimers 15 g,i were also found to have lower affinities than N-H quinolinone dimers 13 g,i conforming that an intact 2 (1H)-pyridone moiety, such as that found in huperzine A, affords maximal affinity in the dimers.

EXAMPLE 10

Cholinesterase Inhibition by Enantiomerically Pure Dimeric Compounds

Cholinesterase assays were carried out using the Ellman method as described in Example 9.

The results of the assays are given in Table III below:

TABLE III

Cholinesterase inhibition by (S,S)- and (R,R)-13 pure enantiomers

| Entry | Drug[a] | n | AChE $IC_{50}(nM)$[b] | BChE $IC_{50}(nM)$[c] | Selectivity for AChE[d] |
|---|---|---|---|---|---|
| 1 | (S,S)-(−)-13g | 10 | 151 ± 36 | 1,820 ± 70 | 12.1 |
| 2 | (S,S)-(−)-13h | 11 | 84 ± 5 | 1,160 ± 80 | 13.8 |
| 3 | (S,S)-(−)-13i | 12 | 52 ± 8 | 9,600 ± 300 | 18.5 |
| 4 | (S,S)-(−)-13j | 13 | 52 ± 9 | 16,700 ± 650 | 321 |
| 5 | (S,S)-(−)-13k | 14 | 240 ± 50 | 59,500 ± 10,100 | 248 |
| 6 | (R,R)-(+)-13i | 12 | 3,130 ± 790 | 297,000 ± 78,400 | 94.9 |
| 7 | (−)-huperzine A[e] | na | 115 ± 1 | 135,000 ± 6,000 | 1,200 |
| 8 | tacrine | na | 231 ± 16 | 77.2 ± 5.8 | 0.3 |

[a]Drugs 13 were assayed as the hydrochloride salts. Elemental analyses matched the proposed salt formulations (C, H, N, Cl ± 0.4%).
[b]Assay performed using rat cornea homogenate, in the presence of ethopropazine as a specific BChE inhibitor.
[c]Assay performed using rat serum, in the presence of BW284c51 as a specific AChE inhibitor.
[d]Selectivity for AChE is defined as $IC_{50}(BChE)/IC_{50}(AChE)$.
[e]Measured $[\alpha]_D^{20} = 149°$ (c = 0.17, CHCl$_3$): literature (ref. 3a): $[\alpha]_D^{25} = 150°$ (c = 0.12, CHCl$_3$).

The 60-fold greater potency of (S,S)-(−)-13i relative to its enantiomer (R,R)-(+)-13i is reminiscent of the 30-fold difference found for the enantiomers of huperzine A, and suggests that the dimers enjoy a multi-point interaction with the AChE active site (Table III, entries 3 & 6). The enantiomerically pure (S,S)-dimers with tether lengths of ten to fourteen methylenes were assayed, and AChE potency was found to be optimized at tether lengths of twelve to thirteen methylenes (Table III, entries 3 and 4). Shorter or longer tethers give inferior inhibition, consistent with simultaneous binding of these drugs to the catalytic and peripheral sites of AChE. Remarkably the most potent drugs (S,S)-(−)-13i–j were twice as potent as (−)-1, the natural product which inspired their synthesis. Kinetic studies using rat cortex AChE farther demonstrated the superior potency of (S,S)-(−)-13i ($k_I$=1 9.6 nM) relative to huperzine A ($K_I$=47.1 nM).

What is claimed is:

1. A dimeric compound comprising two fragments, which may be the same or different, joined together by a divalent linking group, each fragment having a nucleus of the general formula

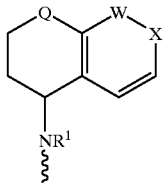

(I)

which may be substituted or unsubstituted, in which Q represents the number of carbon atoms necessary to form a 5,6 or 7-membered ring;

$R^1$ represents a hydrogen atom or an optionally substituted alkyl group;

—W—X— represents a group —N($R^2$)—C(O)— or —N═C(O$R^3$)—, where $R^2$ represents a hydrogen atom or an optionally substituted alkyl, alkenyl, alkynyl or aralkyl group, and $R^3$ represents a hydrogen atom or an optionally substituted alkyl or aralkyl group; or a salt thereof.

2. A compound according to claim 1 in which Q represents one carbon atom which may be substituted or unsubstituted.

3. A compound according to claim 1 in which $R^1$ represents a hydrogen atom or a $C_{1-4}$ alkyl group.

4. A compound according to claim 3 in which $R^1$ represents a hydrogen atom.

5. A compound according to claim 1 in which —W—X— represents a group —N($R^2$)—C(O)—.

6. A compound according to claim 5 in which $R^2$ represents a hydrogen atom or a $C_{1-4}$ alkyl group.

7. A compound according to claim 1 in which —W—X— represents a group —N═C(O$R^3$)—.

8. A compound according to claim 7 in which $R^3$ represents a $C_{1-4}$ alkyl group or a $C_{7-11}$ aralkyl group.

9. A compound according to claim 1 in which the saturated ring of the nucleus of general formula I is substituted at one or more of the available carbon atoms by one or more substituents of formula $R^4$.

10. A compound according to claim 9 in which each substituent $R^4$ independently represents an optionally substituted alkyl or aralkyl group.

11. A compound according to claim 10 in which each substituent $R^4$ independently represents a $C_{1-4}$ alkyl group.

12. A compound according to claim 9 in which two substituents $R^4$ are located at the 7-position of the nucleus of general formula I.

13. A compound according to claim 9 in which one substituent $R^4$ is located at the 5-position of the nucleus of general formula I.

14. A compound according to claim 1 in which the two fragments having a nucleus of general formula I are the same.

15. A compound according to claim 1 in which the two fragments having a nucleus of general formula I are different from one another.

16. A compound according to claim 1 in which the divalent linking group is an optionally substituted alkylene chain which is optionally interrupted by one or more heteroatoms or optionally substituted aryl groups.

17. A compound according to claim 16 in which the optionally substituted alkylene chain is optionally interrupted by one or more moieties selected from —O—, —S—, —NR—, —C(O)— and optionally substituted aryl groups, where R represents a hydrogen atom or an optionally substituted alkyl group.

18. A compound according to claim 16 in which the optionally substituted alkylene chain is optionally interrupted by one or more moieties selected from —O—, —NH—, —C(O)—, phenyl and naphthyl groups.

19. A compound according to claim 16 in which the optionally substituted alkylene chain has a chain length of 2 to 16 atoms.

20. A compound according to claim 16 in which the optionally substituted alkylene chain is an unsubstituted alkylene chain of formula —(CH$_2$)$_n$— in which n is an integer from 4 to 14.

21. A compound according to claim 20 in which n is an integer from 9 to 12.

22. A compound according to claim 1, wherein said compound is N,N'-Di-5'-(5',6',7',8'-tetrahydroquinolin-2-onyl-1,12-diaminododecane or a salt thereof.

23. A compound according to claim 1, wherein said compound is N,N'-Di-5'-(5',6',7',8'-tetrahydroquinolin-2-onyl-1,13-diaminotridecane or a salt thereof.

24. An enantiomer of a compound according to claim 1 or a salt thereof.

25. An (S,S)-enantiomer of a compound according to claim 1 or a salt thereof.

26. An (R,R)-enantiomer of a compound according to claim 1 or a salt thereof.

27. A process for the preparation of a dimeric compound according to claim 1, which comprises reacting two compounds, which may be the same or different, having a nucleus of the general formula

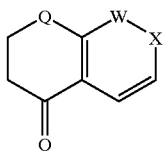

(II)

which may be substituted or unsubstituted, in which Q and —W—X— are as defined in claim 1, or a salt thereof, with a compound of the general formula

HR$^1$N—A—NR$^1$H      (III)

in which each R$^1$ represents a hydrogen atom and an optionally substituted alkyl group and A represents a divalent linking group and, either reducing the bis-imine compound so formed to produce a dimeric compound which is unsubstituted at the 5-position, or reacting the bis-imine compound so formed with a suitable organometallic reagent to produce a dimeric compound which is substituted at the 5-position; and when —W—X— represents a group —N=C(OR$^3$)— and R$^3$ represents an optionally substituted arylmethyl group in at least one of the compounds having a nucleus of general formula II, subjecting the dimeric compound so formed to hydrogenolysis to produce a dimeric compound in which both moieties —W—X— represent a group —N(R$^2$)—C(O)—.

28. A process for the preparation of a dimeric compound according to claim 1, which comprises reacting two compounds, which may be the same or different, having a nucleus of the general formula

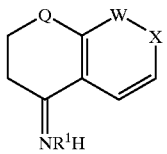

(IV)

which may be substituted or unsubstituted, in which said Q, R$^1$ and —W—X— are as defined in claim 1, or a salt thereof, with a compound of the general formula

L—CO—A$^1$—CO—L      (V)

in which each L independently represents a hydrogen atom or a leaving group Y of which the conjugate acid HY has a pKa value which is less than or equal to 10 and —CO—A$^1$—CO— represents a group which forms a divalent linking group in the resultant dimeric compound; and, if desired, reducing the dimeric compound so formed to produce a further dimeric compound according to claim 1; and, if desired, when —W—X— represents a group —N=C(OR$^3$)— and R$^3$ represents an optionally substituted arylmethyl group in at least one of the compounds having a nucleus of general formula IV, subjecting the dimeric compound so formed to hydrogenolysis to produce a dimeric compound in which both moieties —W—X— represent a group —N(R$^2$)—C(O)—.

29. A process according to claim 28 in which each L independently represents a hydrogen or chlorine atom.

30. A process according to claim 28 in which both moieties —W—X— represent a group —N=C(OR$^3$)—.

31. A process according to claim 28, in which at least one of the compounds having a nucleus of general formula IV is substituted at the 5-position by said substituent R$^4$.

32. A pharmaceutical composition comprising a carrier and, as active ingredient, a dimeric compound as defined in claim 1.

33. A process for the preparation of a pharmaceutical composition which comprises bringing a dimeric compound as defined in claim 1 into association with a carrier.

34. A method of using the dimeric compound according to claim 1 as a cholinesterase inhibitor.

35. A method of using the dimeric compound according to claim 1 in the treatment of a condition which is ameliorated by cholinesterase inhibition.

36. A method of using the dimeric compound according to claim 34 in which the cholinesterase is acetylcholinesterase (AChE).

37. A method of using the dimeric compound according to claim 34 in which the cholinesterase is butyrylcholinesterase (BChE).

38. A method of using the dimeric compound according to claim 1 in the treatment of a neurodegenerative disease.

39. A method of using the dimeric compound according to claim 38 in which the neurodegenerative disease is selected from Alzheimer's Disease and myasthenia gravis.

40. A method for inhibiting cholinesterase activity in a mammal afflicted with a condition which is ameliorated by cholinesterase inhibition which comprises administering to the mammal in need thereof an amount of a compound according to claim 1, effective to inhibit said activity.

41. A method according to claim 40 in which the cholinesterase is acetylcholinesterase (AChE).

42. A method according to claim 40 in which the cholinesterase is butyryl cholinesterase (BChE).

43. A method of treating a neurodegenerative disease in a mammal which comprises administering to said mammal a therapeutically effective amount of a compound according to claim 1.

44. A method according to claim 43 in which the neurodegenerative disease is selected from Alzheimer's Disease and myasthenia gravis.

45. A method of using the pharmaceutical composition according to claim 32 as a cholinesterase inhibitor.

46. A method of using the pharmaceutical composition according to claim 32 in the treatment of a condition which is ameliorated by cholinesterase inhibition.

47. A method of using the pharmaceutical composition according to claim 32 in the treatment of neurodegenerative disease.

48. The method of using the dimeric compound according to claim 1, for manufacturing a medicament used as a cholinesterase inhibitor.

49. The method of using the pharmaceutical composition according to claim 32, for manufacturing a medicament used as a cholinesterase inhibitor.

50. The method of using the dimeric compound according to claim 1, for manufacturing a medicament for use in the treatment of a condition which is ameliorated by cholinesterase inhibition.

51. The method of using the pharmaceutical composition according to claim 32, for the manufacturing of a medicament for use in the treatment of a condition which is ameliorated by cholinesterase inhibition.

52. The method for using the dimeric compound according to claim 48, wherein cholinesterase is butyrylcholinesterase (BChE).

53. The method for using the dimeric compound according to claim 48, wherein cholinesterase is butyrylcholinesterase (BChE).

54. The method for using the dimeric compound according to claim 1 for the manufacture of a medicament for use in the treatment of a neurodegenerative disease.

55. The method for using the pharmaceutical composition according to claim 32, for the manufacture of a medicament for use in the treatment of a neurodegenerative disease.

56. The method according to claim 54, wherein said neurodegenerative disease is selected from Alzheimer's Disease and myasthenia gravis.

* * * * *